United States Patent
Taskaev et al.

(10) Patent No.: US 12,035,457 B2
(45) Date of Patent: Jul. 9, 2024

(54) SYSTEMS, DEVICES, AND METHODS FOR DEFORMATION REDUCTION AND RESISTANCE IN METALLIC BODIES

(71) Applicant: TAE Technologies, Inc., Foothill Ranch, CA (US)

(72) Inventors: Sergey Y. Taskaev, Novosibirsk (RU); Alexandr N. Makarov, Novosibirsk (RU); Evgeniia O. Sokolova, Novosibirsk (RU)

(73) Assignee: TAE Technologies, Inc., Foothill Ranch, CA (US)

( * ) Notice: Subject to any disclaimer, the term of this patent is extended or adjusted under 35 U.S.C. 154(b) by 0 days.

(21) Appl. No.: 17/383,188

(22) Filed: Jul. 22, 2021

(65) Prior Publication Data
US 2022/0030696 A1     Jan. 27, 2022

(30) Foreign Application Priority Data
Jul. 23, 2020  (RU) ............................ RU2020124384

(51) Int. Cl.
| H05H 6/00 | (2006.01) |
| A61N 5/10 | (2006.01) |
| G21B 1/17 | (2006.01) |
| G21B 1/19 | (2006.01) |
| H05H 5/06 | (2006.01) |

(52) U.S. Cl.
CPC ............ *H05H 6/00* (2013.01); *A61N 5/1077* (2013.01); *A61N 2005/1022* (2013.01); *A61N 2005/109* (2013.01); *H05H 5/063* (2013.01); *H05H 2277/11* (2013.01)

(58) Field of Classification Search
CPC ... H05H 3/06; H05H 6/00; G21G 4/02; G21B 1/19
See application file for complete search history.

(56) References Cited

U.S. PATENT DOCUMENTS

| 2011/0091000 A1 | 4/2011 | Stubbers et al. |
| 2016/0333918 A1 | 11/2016 | Neal et al. |

FOREIGN PATENT DOCUMENTS

RU         2326513 C2     6/2008

OTHER PUBLICATIONS

Astrelin et al., "Blistering of the selected materials irradiated by intense 200keV proton beam," Journal of Nuclear Materials, 396(1):43-48, (Jan. 1, 2010).
Badrutdinov et al., "In Situ Observations of Blistering of a Metal Irradiated with 2-MeV Protons," Metals, 7:558, (2017).
Brown et al., "Development of a high-power neutron-producing lithium target for boron neutron capture therapy," Proceedings of SPIE, 4142:81-91, (Dec. 18, 2000).
Guseva et al., "Radiation blistering," Sov. Physics Usp., 24(12):996-1007, (Dec. 1, 1981).

(Continued)

*Primary Examiner* — Jon Eric C Morales
(74) *Attorney, Agent, or Firm* — ALSTON & BIRD LLP

(57) ABSTRACT

Metallic bodies are provided having a lithium layer and a metallic substrate. The metallic bodies can exhibit increased resistance to radiation-induced deformations such as blistering. Methods are provided for transitioning the metallic bodies into more blister resistant configurations, as our methods for diminishing or eliminating blisters previously formed. Systems for utilizing the metallic bodies and methods are also disclosed.

57 Claims, 18 Drawing Sheets

(56) References Cited

OTHER PUBLICATIONS

Phoenix et al., "Development of a higher power cooling system for lithium targets," Applied Radiation and Isotopes, 106:49-52, (2015).
WIPO Application No. PCT/US2021/042717, PCT International Search Report and Written Opinion dated Nov. 12, 2021.
Taskaev et al, "Boron Neutron Capture Therapy," Chapter 3, Accelerator-based Neutron Sources, Novosibirsk, Publishing House of Siberian Branch of the Russian Academy of Sciences, (2016), English Translation only.
Bayanov et al., "Neutron producing target of the accelerator based neutron source for neutron-capture therapy," Institute of Nuclear Physics, 2004-4, Novosibirsk, pp. 3-5, 8, 19-21, (2005), English translation.
Neutron sources at http://nuclphys.sinp.msu.ru/experiments/neutrgen/index.html, uploaded on Jul. 29, 2019.
Mikhailovich, "Modification of the surface of a lithium target when exposed to a proton beam with energy of 2 MeV," Graduation thesis, Novosibirsk, pp. 5-6, 9, 18, 26, (2019), English Translation.
RU 2020124384/28 Search report mailed Aug. 30, 2023, English Translation only.
RU 2020124384/28 Official Notification mailed Nov. 23, 2023, English Translation only.

SYSTEMS, DEVICES, AND METHODS FOR DEFORMATION REDUCTION AND RESISTANCE IN METALLIC BODIES

CROSS-REFERENCE TO RELATED APPLICATIONS

The present application claims priority to Russian Patent Application No. 2020124384, titled "SYSTEMS, DEVICES, AND METHODS FOR DEFORMATION REDUCTION AND RESISTANCE IN METALLIC BODIES," filed Jul. 23, 2020, the contents of which are incorporated herein by reference in their entirety for all purposes.

FIELD

The subject matter described herein relates generally to systems, devices, and methods for reducing the likelihood of deformation formation and/or diminishing the size of deformations in metallic bodies.

BACKGROUND

There are many applications where metallic bodies are placed in environments subjected to relatively large amounts of charged particle radiation. Examples of these applications include medical treatment (e.g., cancer) and diagnostics, nuclear fusion, space technology, isotope production, hazardous materials detection, the assaying of precious metal ores, imaging, and others.

Exposure to a sufficient amount of charged particle radiation can cause certain types of metallic bodies to undergo a potentially degradative condition where the radiation induces the generation of deformations within the body. These deformations often take the form of blisters, and the condition giving rise to such is commonly referred to as blistering. Blistering can be caused by the formation of molecular hydrogen gas within these metallic bodies. The hydrogen gas can be formed as the charged particle radiation, such as proton radiation, recombines with metal electrons to form molecular hydrogen gas. The gas can accumulate in a pocket (e.g., a nascent bubble) within the metallic body. Continued exposure to the radiation can produce additional hydrogen that causes the gaseous pocket to grow and potentially manifest itself as a blister (e.g., a crack, bump, flake, and/or other deformation) on or near the surface of the metallic body. This form of blistering is more commonly characteristic of metals that poorly dissolve hydrogen (e.g., copper, aluminum, molybedenum, iron, silver, tungsten, platinum, and gold) than metals that dissolve hydrogen well (e.g., alkali, alkaline-earth, titanium, tantalum, niobium, vanadium, nickel, and palladium). (See, e.g., Badrutdinov et al., In Situ Observations of Blistering of a Metal Irradiated with 2-MeV Protons, Metals 2017, 7, 558.)

The material deformation caused by such blisters can be significant and, depending on the type of application, can lead to problems. As such, blistering is generally considered an undesirable effect of charged particle radiation exposure.

Accordingly, needs exist for systems, devices, and methods with anti-deformation characteristics, such as those that resist blister formation, reduce the likelihood of blister formation, and/or diminish the size of blisters already formed in metallic bodies exposed to charged particle radiation.

SUMMARY

Provided herein are example embodiments of systems and devices exhibiting improved anti-deformation characteristics when subjected to charged particle radiation, and methods for engendering those characteristics into the systems and devices. These anti-deformation characteristics can include increased resistance to deformation formation or reduced likelihood of deformation formation when subjected to the radiation. These methods also include embodiments that diminish the size of deformations already formed from radiation exposure and that can diminish the number of deformations already formed. Methods of manufacturing systems and devices exhibiting these improved anti-deformation characteristics are also provided, as our methods of conditioning manufactured systems and devices such that they exhibit these improved characteristics. Examples of the deformations can include, but are not limited to, blisters induced by the formation of hydrogen gas. Examples of benefits from the aforementioned embodiments can include prevention of deformation formation, mitigating the effect of (e.g., healing or alleviating) deformations already formed, lengthening the operating life of systems and devices subjected to charged particle radiation, and others.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The metallic bodies that are the subject of the embodiments disclosed herein can be used in any of a broad range of applications (e.g., industrial, commercial, research, or otherwise) and, accordingly, can have any of a broad range of shapes, sizes, or configurations that suit the needs of those applications. The metallic bodies disclosed herein include at least a lithium layer and a metallic substrate. The metallic substrate can be composed primarily of one metallic element (e.g., a copper substrate with a high purity), an alloy of two or more metallic elements, a compound of one or more metallic elements with one or more non-metallic elements, or others. Examples of metals for substrate 104 include, but are not limited to: copper, aluminum, molybdenum, iron, silver, palladium, tantalum, carbon (e.g., graphite and diamond phases), tungsten, platinum, or gold. The lithium layer can likewise be composed primarily of lithium, can be a lithium alloy or compound, or otherwise. The lithium layer can be in either solid or liquid form. In the embodiments described herein, the lithium layer can be composed of one or more lithium isotopes. For example, in the embodiments described herein, the lithium layer can be composed of at least 90% lithium-7 (7Li), at least 92% lithium-7, at least 95% lithium-7, at least 98% lithium-7, at least 99% lithium-7, at least 99.9% lithium-7, and the like. The remainder can be lithium-6 isotope (6Li), another lithium isotope, impurities, or another element (e.g., as in a lithium compound).

Figure 1A:
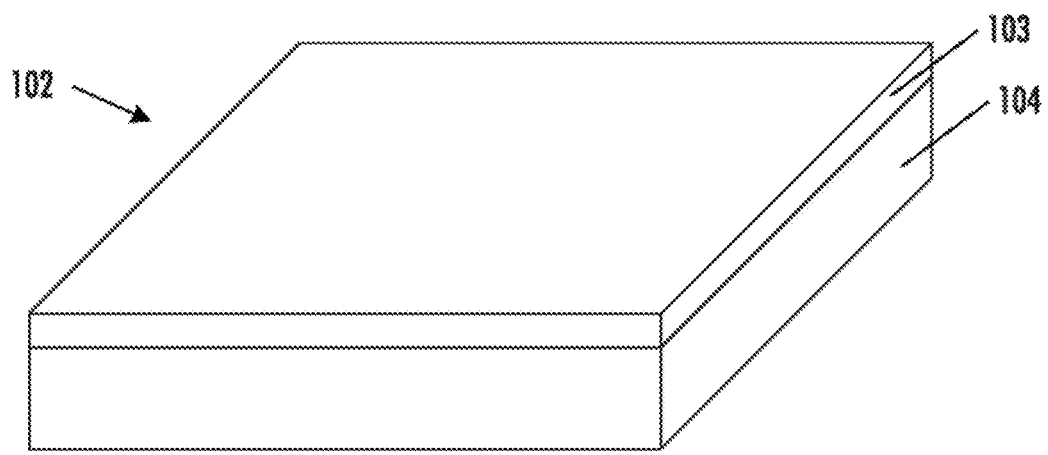
FIGS. 1A, 1B, 1C, and 1D are perspective views depicting example embodiments of a metallic body.
Figure 1B:
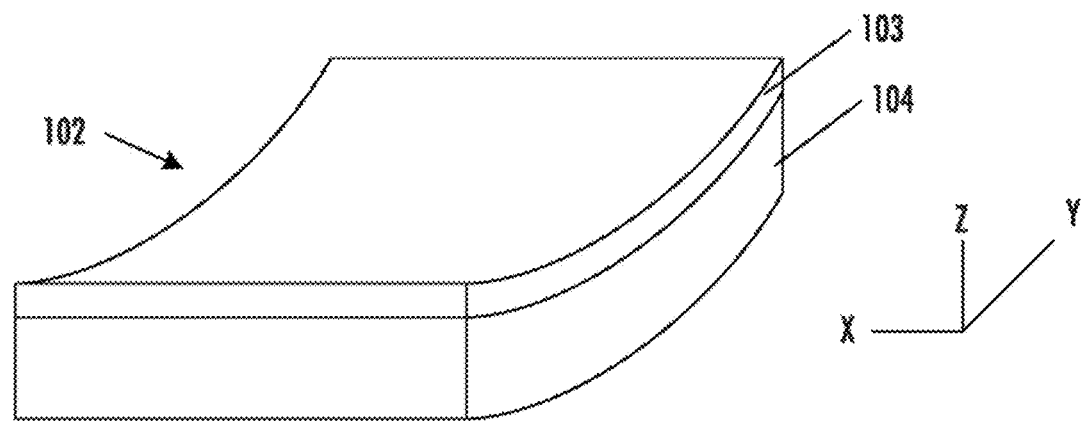
Figure 1C:
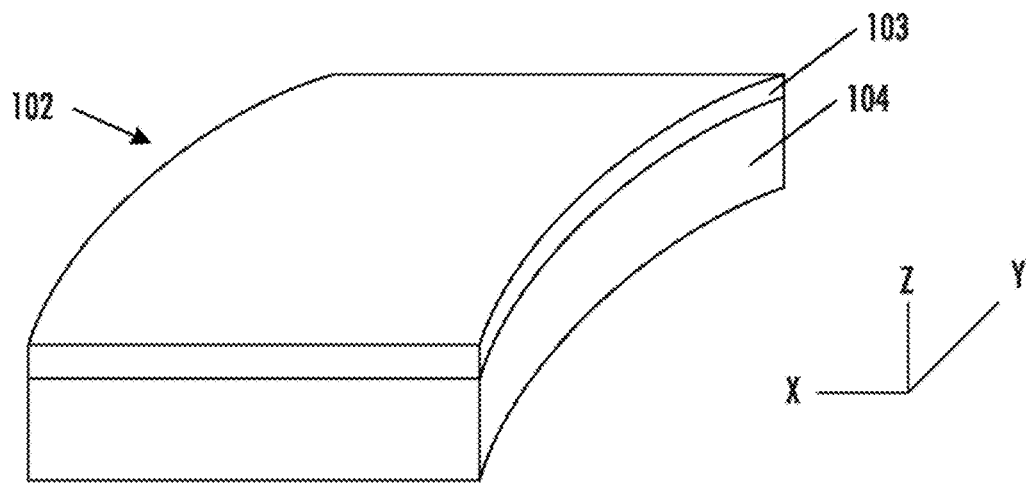

FIGS. 1A-1C are perspective views depicting example embodiments of a metallic body 102 having a lithium layer 103 and a metallic substrate 104. While lithium layer 103 is shown as having an exposed surface (e.g., at top in these views), lithium layer 103 can also be embedded within metallic body 102 such that it does not form an outermost surface of body 102. Likewise, while substrate 104 is shown as a bulk substrate having an exposed surface (e.g., at bottom), substrate 104 can also be embedded within body 102 such that it does not form an outermost surface (e.g., by inclusion of other structures or materials in body 102).

In FIG. 1A, metallic body 102 has a planar or flat form. In FIG. 1B metallic body 102 has a concave form exhibiting curvature in the Y-Z plane, and in FIG. 1C metallic body 102 has a convex form exhibiting curvature in the Y-Z plane. Concave and convex forms are denoted from the perspective of the reader. FIGS. 1A-1C depict some basic examples of shapes and surface contours that characterize metallic body 102. Metallic body 102 can have more complex shapes and surface contours, including ones that combine two or more of the shapes and surface contours depicted in FIGS. 1A-1C, or ones that are different and/or more complex. The bodies 102 shown in FIGS. 1A-1C can represent the entire physical extent of the body 102 or can represent a portion or a section of a still larger metallic body. A list of example three-dimensional shapes for body 102 includes, but is not limited to: a plate or plating, a disc, a strut, a cube or portion thereof, a cuboid or portion thereof, a cylinder or portion thereof, a prism or portion thereof, a cone or portion thereof, a pyramid or portion thereof, a sphere or portion thereof, a toroid or portion thereof, a hollow chamber or portion thereof, any combination of two or more of the foregoing, and others.

FIGS. 2A-2F depict an example embodiment of metallic body 102 having lithium layer 103 on or adjacent to metallic substrate 104 during various stages of exposure to charged particle radiation. While body 102 is depicted here as being planar (flat), the mechanisms described with respect to these figures are equally applicable to all shape and size configurations of body 102 discussed or encompassed herein.

Figure 2A:
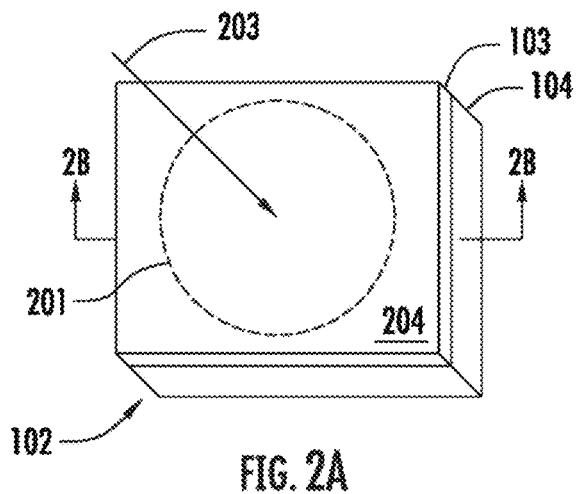
FIG. 2A is a perspective view depicting an example embodiment of a metallic body during exposure to charged particle radiation at a first time.
Figure 2B:
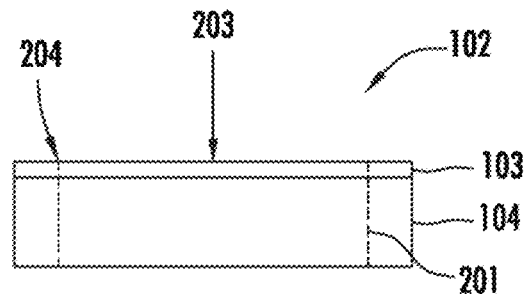
FIG. 2B is a cross-sectional view depicting the example embodiment taken across line 2B-2B of FIG. 2A.

FIG. 2A is a perspective view depicting metallic body 102 with a region 201 of surface 204 during exposure to charged particle radiation at a first time. FIG. 2B is a cross-sectional view depicting body 102 taken across line 2B-2B of FIG. 2A. The incident direction of the charged particle radiation is indicated by vector 203, which in this example is normal to surface 204. In this embodiment, the fluence (the flux integrated over time, where flux is particles per unit area at an instant in time) is constant across region 201 (e.g., the entire surface region 201 is exposed to a uniform distribution of charged particle radiation simultaneously, or a beam of charged particle radiation having a cross-sectional area smaller than that of region 201 is moved across region 201 in a uniform manner as will be described herein). At this first time of FIGS. 2A and 2B, no blistering has occurred in metallic body 102.

Figure 2C:
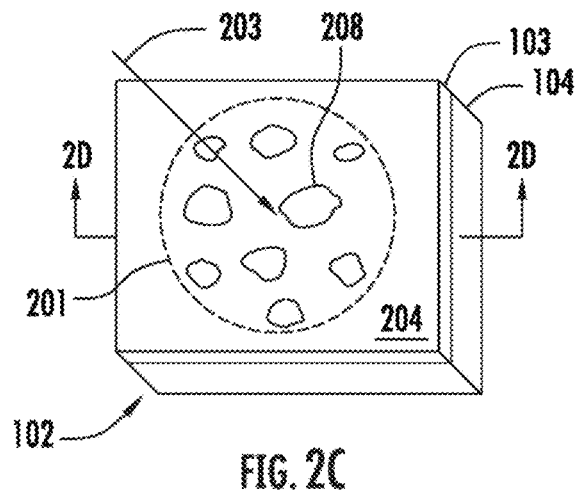
FIG. 2C is a perspective view depicting an example embodiment of a metallic body during exposure to charged particle radiation at a second time.
Figure 2D:
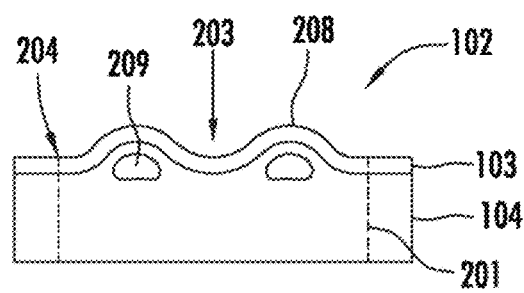
FIG. 2D is a cross-sectional view depicting the example embodiment taken across line 2D-2D of FIG. 2C.

FIG. 2C is another perspective view depicting body 102, and FIG. 2D is a cross-sectional view depicting body 102 taken across line 2D-2D of FIG. 2C. Exposure of region 201 to additional, prolonged charged particle radiation has resulted in the formation of deformations 208, which in this example are blisters. The visual appearance and mechanism of formation of blisters 208 may vary. In this example, formation of gaseous pockets 209 in substrate 104 has deformed the surrounding material, manifesting as blisters (e.g., deviations in surface contour, raised surface formations, bumps, cracks, etc.) visible in region 201 of surface 204.

The blistering threshold (e.g., the dose at which blistering commences) is dependent on various factors, such as the type of metal substrate, the sample temperature during irradiation, the type of radiation (e.g., ion, proton), the energy of the radiation, and others. Prior studies such as Badrutdinov et al., "In Situ Observations of Blistering of a Metal Irradiated with 2-MeV Protons" Metals 2017, 7, 558, have noted that the blistering threshold of a copper surface depends on the copper purity and that the purer the copper, the higher the threshold is. Batrutdinov notes that for proton energies of 2 megaelectronvolts (MeV), copper's maximum threshold is $3 \times 10^{19}$ cm$^{-2}$ and the minimum value can be seven times lower. Also, the size of the blisters on the copper surface depends on the copper purity, where the purer the copper, the larger the blisters are. Copper blister sizes resulting from 2 MeV proton radiation can range from 40±20 microns to 160±50 microns. FIGS. 2G and 2H are images depicting an example of a blister on the surface of 99.99996% coarse copper, before and after being cut by an ion beam. The gaseous pocket is visible inside the cut blister in FIG. 2H.

Figure 2E:
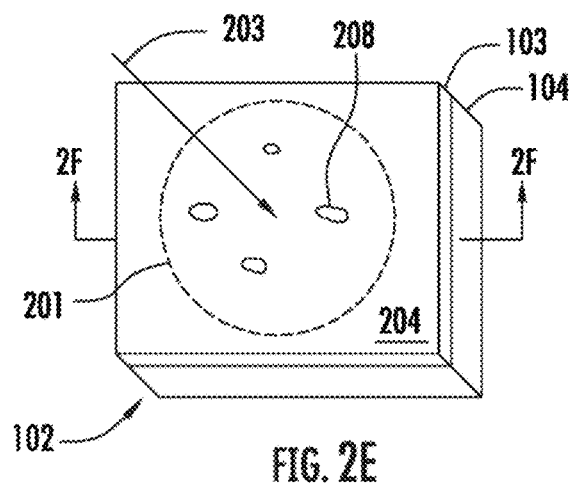
FIG. 2E is a perspective view depicting an example embodiment of a metallic body during exposure to charged particle radiation at a third time.
Figure 2F:
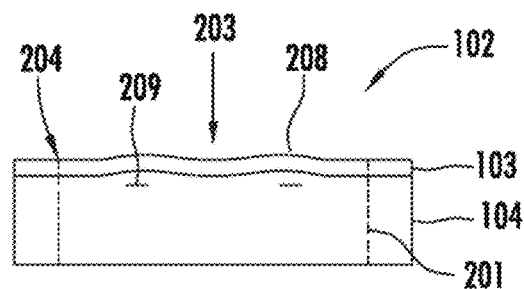
FIG. 2F is a cross-sectional view depicting the example embodiment taken across line 2F-2F of FIG. 2E.
Figure 2G:
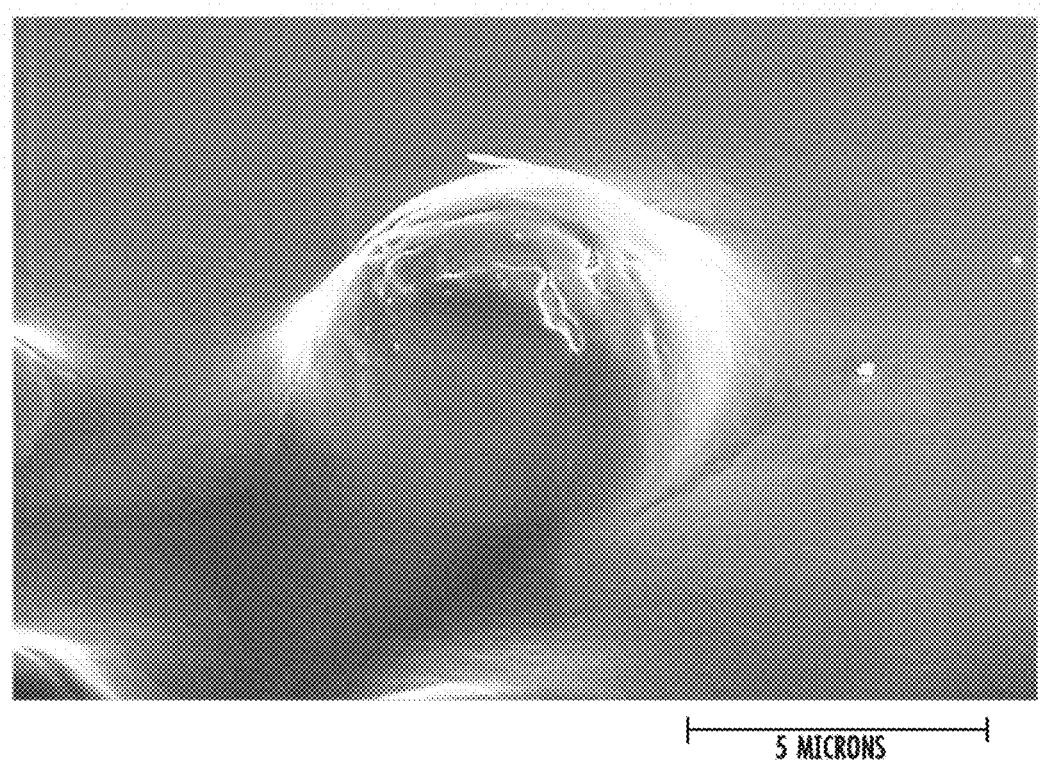
FIGS. 2G and 2H are images depicting an example of a blister on the surface of coarse copper, before and after being cut by an ion beam, respectively.
Figure 2H:
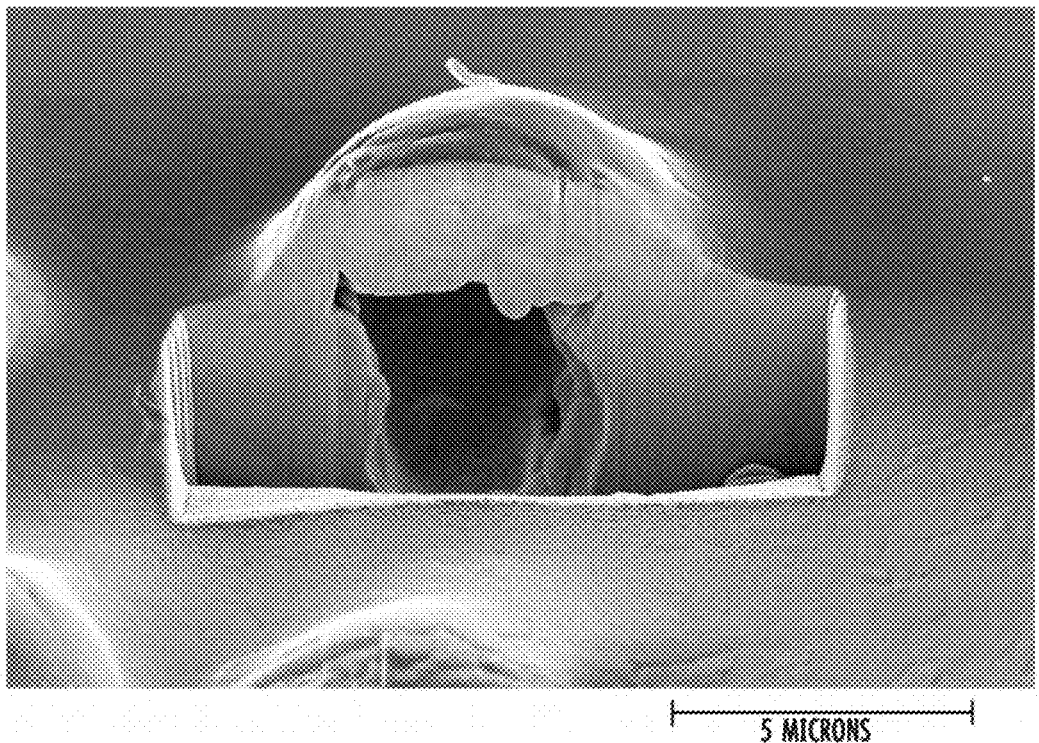

FIG. 2E is another perspective view depicting metallic body 102, and FIG. 2F is a cross-sectional view depicting body 102 taken across line 2F-2F of FIG. 2E. After formation of blisters 208, exposure of region 201 to still further charged particle radiation has diminished or reduced the size of blisters 208. FIG. 2F shows that the volume of gaseous pockets 209 is diminished as compared to FIG. 2D, which has in turn diminished the height of blisters 208 (FIG. 2F as compared to FIG. 2D) and the surface area of the raised portions of blisters 208 (FIG. 2E as compared to FIG. 2C).

The application of charged particle radiation in this embodiment, at least to the point where blister reduction begins, results in a metallic body 102 with enhanced resistivity to blister formation. As radiation is applied past this point, blisters 208 continue to diminish, and the resistivity to blister formation is increased still further. Thus a metallic body 102 subjected to the process described with respect to FIGS. 2A-2F undergoes a form of material conditioning that enhances its resistance to further blister formation.

Figure 1D:
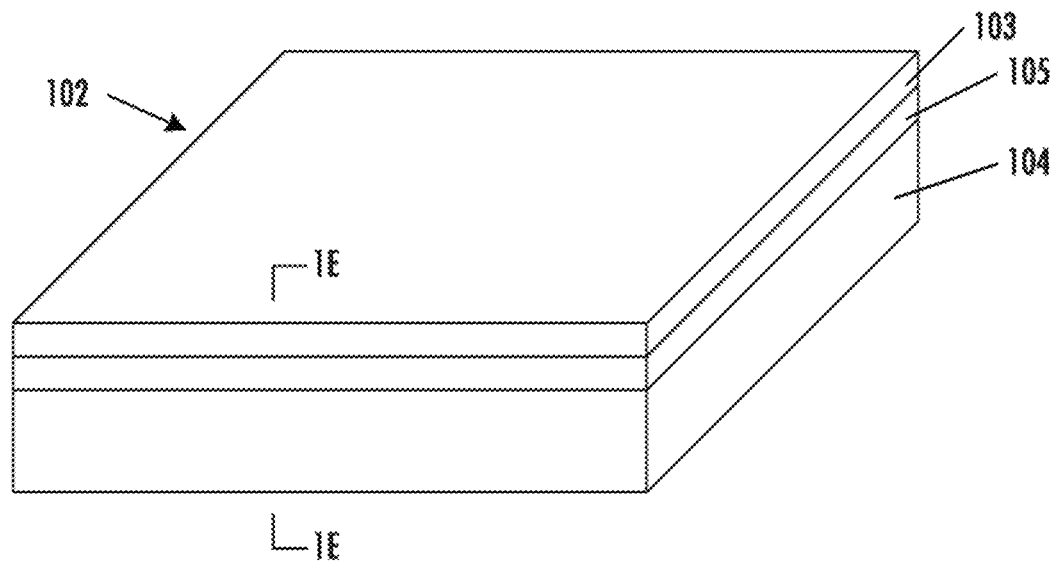
Figure 3:
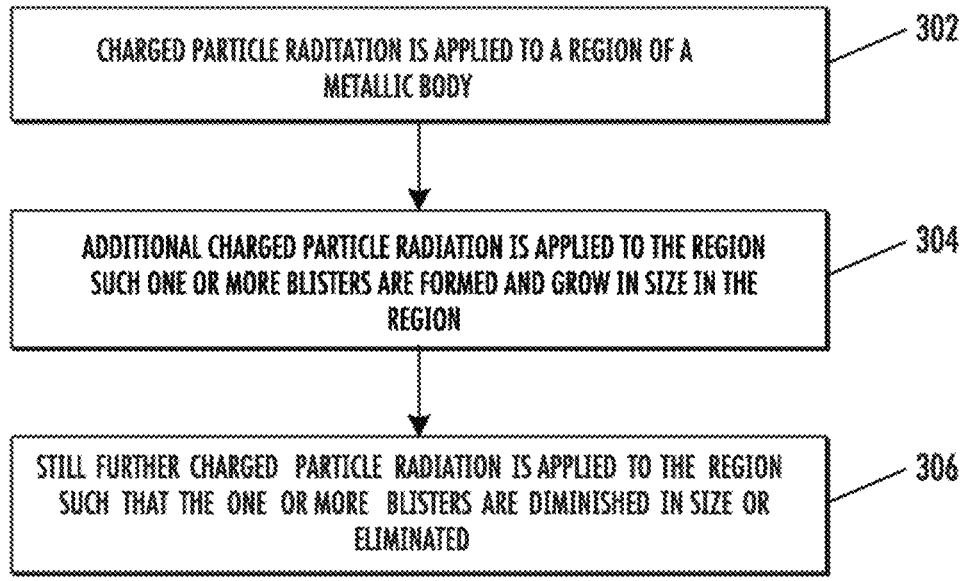
FIG. 3 is a flow chart depicting an example embodiment of a method of diminishing blisters in a metallic body.

FIG. 3 is a flow chart depicting an example embodiment of a method 300 in accordance with the process described with respect to FIGS. 2A-2F. At step 302, charged particle radiation is applied to a region of metallic body 102 (e.g., having lithium as described with respect to FIGS. 2A-2B). At step 304, additional charged particle radiation has been applied such that one or more blisters are formed and grow in size in the region (e.g., as described with respect to FIGS. 2C-2D). At step 306, still further charged particle radiation is applied such that the one or more blisters are diminished in size. Step 306 can continue until blister size reduction substantially stops, until some or all blisters are eliminated, or continuously after elimination of the blisters, depending on the application. The interval between steps 304 and 306, in some embodiments, may include a phase where blister formation in the region ceases or substantially ceases (or blister size growth in the region ceases or substantially ceases), but blister size reduction does not yet occur. Further application of charged particle radiation Lithium layer 103 can be in direct contact with metallic substrate 104 as depicted in FIGS. 1A-1C. In certain embodiments described herein, a compound can form or be located between lithium layer 103 and metallic substrate 104. FIG. 1D is a perspective view depicting a planar metallic body 102 with lithium layer 103, metallic substrate 104, and a lithium-metal compound layer 105 located between 103 and 104. That compound can include lithium (from layer 103) and one or more metals of the metallic substrate 104. For example, when substrate 104 is copper, then layer 105 can be a lithium-copper compound (e.g., LiCu). The formation of this compound layer 105 may be induced by interaction of body 102 with the charged particle radiation itself, by heat produced from the charged particle radiation (or by nuclear reactions induced by the radiation), or by other mechanisms. In embodiments where metallic substrate 104 is itself a layered structure, the lithium compound layer 105 can form between lithium layer 103 and the most adjacent layer of metallic substrate 104.

Figure 1E:
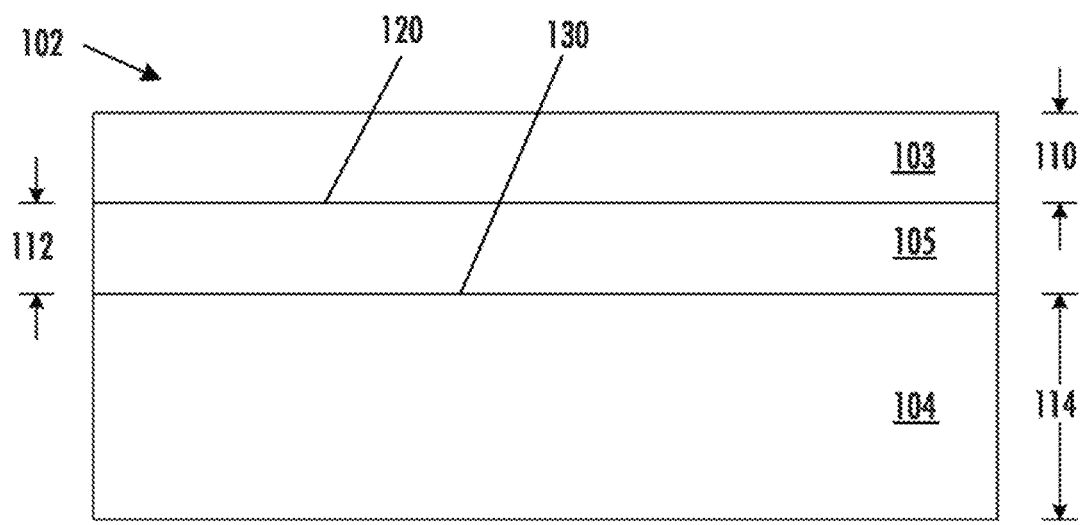
FIG. 1E is a cross-sectional view depicting an example embodiment of a metallic body taken along a section of line 1E-1E of FIG. 1D.

FIG. 1E is a cross-sectional view depicting this example embodiment taken along a section of line 1E-1E of FIG. 1D. As labeled in FIG. 1E, lithium layer 103 has a thickness 110, lithium compound layer 105 has a thickness 112, and substrate 104 has a thickness 114. The relative thicknesses here are for example only. While substrate 104 will generally be the thickest layer in most embodiments, such is not required. The transition 120 between lithium layer 103 and lithium compound layer 105 can be immediate or gradual, as can the transition 130 between lithium compound layer 105 and substrate 104.

FIGS. 4A-4G depict another example embodiment of metallic body 102 at various stages of charged particle radiation exposure. As with the embodiment of FIGS. 2A-2F, body 102 is depicted here as being planar (flat), but the subject matter described with respect to these figures is equally applicable to all shape and size configurations of body 102 discussed or encompassed herein. A lithium compound layer 105 is formed during the sequence of operations depicted in FIGS. 4A-4G. In these embodiments (and those of FIGS. 5 and 9B, etc.), the mechanism by which blister size reduction and elimination occurs is the formation of the lithium compound layer; however, the embodiments described herein are not limited to such (e.g., as demonstrated by the embodiments of FIGS. 3, 7, 9A, and 9C) and the scope of the subject matter set forth herein covers other mechanisms as well.

Figure 4A:
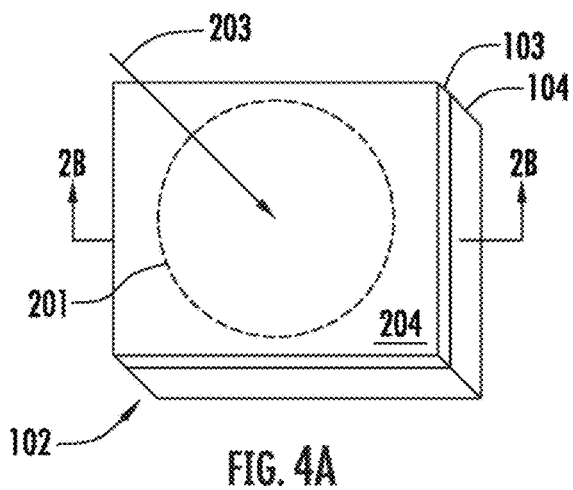
FIG. 4A is a perspective view depicting an example embodiment of a metallic body during exposure to charged particle radiation at a first time.
Figure 4B:
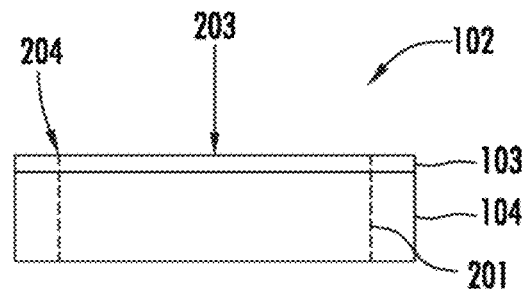
FIG. 4B is a cross-sectional view depicting the example embodiment taken across line 4B-4B of FIG. 4A.

FIG. 4A is a perspective view depicting metallic body 102 with a region 201 of surface 204 being exposed to charged particle radiation at a first time. FIG. 4B is a cross-sectional view depicting body 102 taken across line 4B-4B of FIG. 4A. FIGS. 4A-4B are similar to FIGS. 2A-2B, respectively. The incident direction of the charged particle radiation is indicated by vector 203, which in this example is normal to surface 204. In this embodiment, the fluence is constant across region 201 (e.g., the entire surface region 201 is exposed to a uniform distribution of charged particle radiation simultaneously, or a beam of charged particle radiation having a cross-sectional area smaller than that of region 201 is moved across region 201 in a uniform manner as will be described herein). At this first time of FIGS. 4A and 4B, no blistering has occurred in metallic body 102.

Figure 4C:
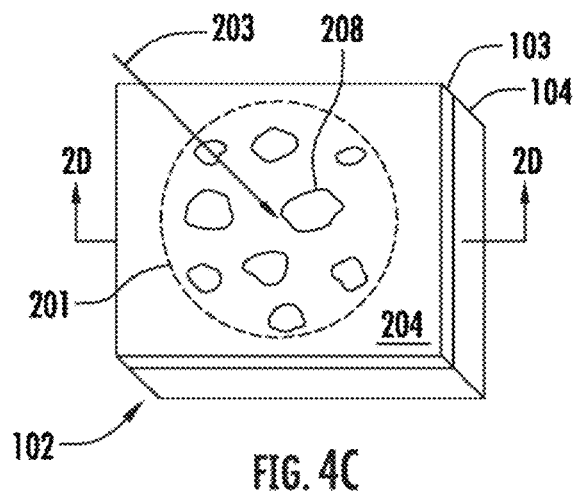
FIG. 4C is a perspective view depicting an example embodiment of a metallic body during exposure to charged particle radiation at a second time.
Figure 4D:
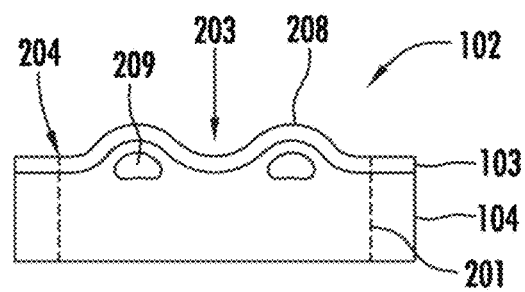
FIG. 4D is a cross-sectional view depicting the example embodiment taken across line 4D-4D of FIG. 4C.
Figure 4E:
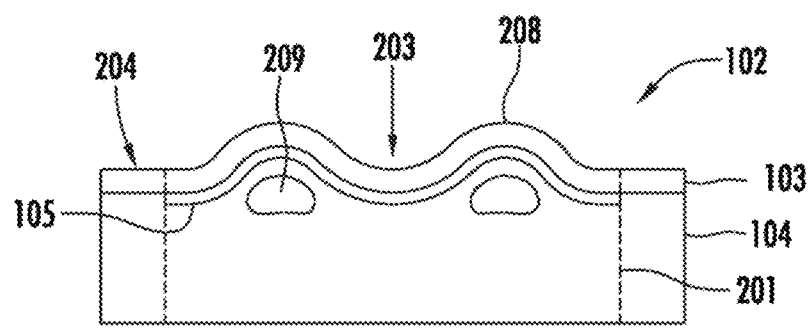
FIG. 4E is a cross-sectional view depicting an example embodiment with a partially formed compound layer.

FIG. 4C is another perspective view depicting metallic body 102, and FIG. 4D is a cross-sectional view depicting metallic body 102 taken across line 4D-4D of FIG. 4C. Exposure of region 201 to additional, prolonged charged particle radiation has resulted in the formation of blisters 208. The visual appearance and mechanism of formation of the blisters 208 may vary. In this example, the formation of gaseous pockets 209 in substrate 104 has deformed the surrounding material, manifesting as deformations (e.g., deviations in surface contour, raised surface formations, bumps, cracks, etc.) visible in region 201 of surface 204. At the stages depicted in FIGS. 4A-4D, either no lithium compound layer has yet been formed, or any lithium compound layer that has been formed is not of sufficient thickness to prevent blister formation or prevent blister formation, as depicted in FIG. 4E.

Figure 4F:
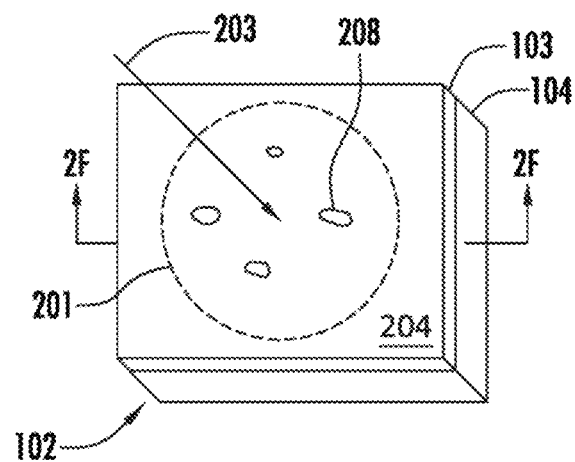
FIG. 4F is a perspective view depicting an example embodiment of a metallic body during exposure to charged particle radiation at a third time.
Figure 4G:
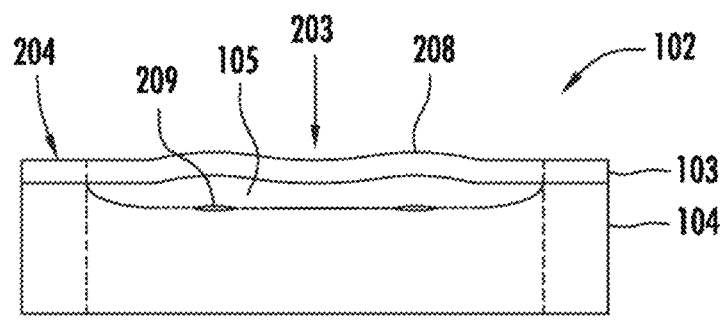
FIG. 4G is a cross-sectional view depicting the example embodiment taken across line 4G-4G of FIG. 4F.

FIG. 4F is another perspective view depicting metallic body 102, and FIG. 4G is a cross-sectional view depicting body 102 taken across line 4G-4G of FIG. 4F. Here, after formation of blisters 208, exposure of region 201 to still further charged particle radiation has resulted in the formation of a lithium compound layer 105 of sufficient size (e.g., depth 402 in FIG. 4G) within region 201 to cause the size of blisters 208 to be reduced or diminished. In certain implementations it is desirable to form compound layer 105 such that the sufficient size is present with uniformity across the relevant portion of body 102 (e.g., existence across the entirety of region 201). FIG. 4G shows that, in this example, the depth of lithium compound layer 105 has reached gaseous pockets 209, or is in close proximity to gaseous pockets 209, so as to permit the gas within pocket 209 to diffuse through layers 105 and 103 and out of body 102. Lithium-copper compound layer 105 has an increased diffusivity to hydrogen gas as compared to copper alone, and thus permits hydrogen gas in the volume of pockets 209 to diffuse outwards and escape. As a result, the size of pockets 209 has diminished as compared to FIG. 4D, which has in turn diminished the height of the raised portions blisters 208 (FIG. 4G as compared to FIG. 4D) and the surface area of the raised portions of blisters 208 (FIG. 4F as compared to FIG. 4C).

Because the visual appearance and mechanism of formation of blisters 208 may vary, the manners in which blisters are diminished may also vary. Examples of a blister 208 being diminished in size includes reduction in the exposed surface area of blister 208 on surface 204, reduction in the height of a blister 208 (as measured relative to the height of the adjacent unblistered surface or relative to the height of the surface prior to blistering), reduction in the height or volume of a gaseous pocket 209, reduction in the size (width or length) of a crack in surface 204, reduction in the height of a flake of material deflected from surface 204, and others. Blisters 208 in the form of raised bumps (e.g., FIGS. 2C-2D and FIGS. 4C-4D) can also be substantially eliminated, such that diminishing of blisters results in a reduction of the overall count of blisters 208 in a particular region of body 102.

The application of charged particle radiation in the embodiment of FIGS. 4A-4G, at least to the point where a lithium compound layer 105 of sufficient size to permit blister reduction is created, results in a metallic body 102 with enhanced resistivity to blister formation. As radiation is applied past this point, blisters 208 continue to diminish, and the resistivity to blister formation is increased still further. Thus a metallic body 102 subjected to the process described with respect to FIGS. 4A-4G undergoes a form of material conditioning that enhances its resistance to the formation of blisters.

Blisters are generally formed in the bulk of the material where the incident particle stops. For particles of the same energy, the range of travel will generally follow a probabilistic distribution (e.g., Gaussian), and will increase with energy. The projected range is mainly dependent on the material and the energy and type of the incident particle. For example, protons having an energy of 2 MeV incident on different materials will have an approximate projected range according to Table 1.

TABLE 1

| Material | Approx. Projected Range (microns) |
| --- | --- |
| Aluminum | 44 |
| Beryllium | 50 |
| Carbon | 38 |
| Copper | 19 |
| Iron | 20 |
| Lithium | 160 |
| Molybdenum | 18 |
| Tantalum | 17 |
| Titanium | 30 |
| Tungsten | 14 |
| Vanadium | 23 |

The addition of a lithium layer 103 above a non-lithium bulk substrate will slow the incident particles somewhat and lessen the stopping distances of Table 1. Table 1 is useful in demonstrating the relative differences in thickness at which blisters occur in bulk materials, and is instructive in how thick a compound layer 105 should be in relative terms in order to reach the particle projected range.

Figure 5:
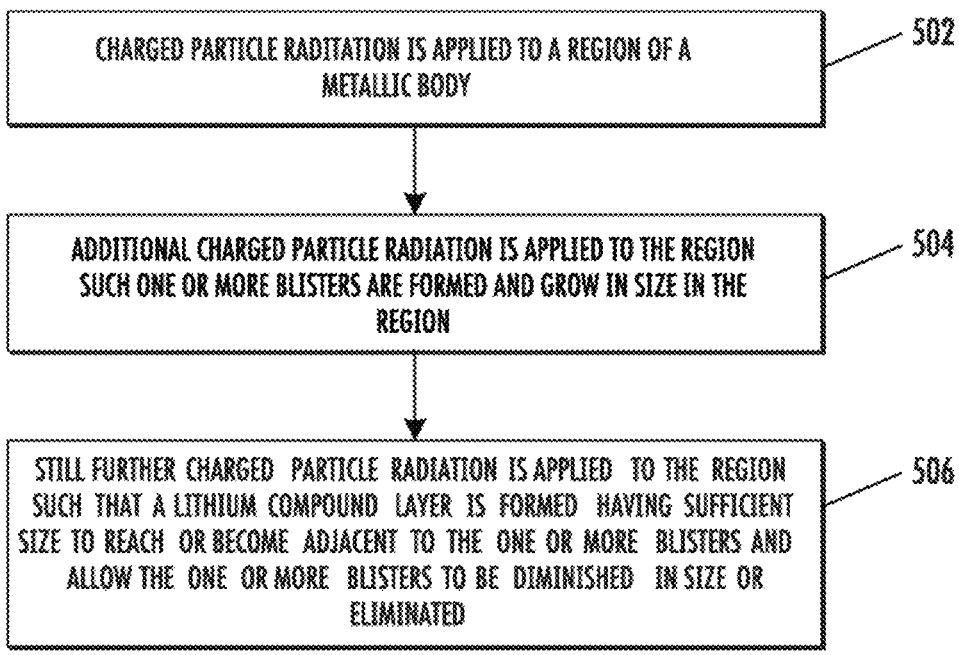
FIG. 5 is a flow chart depicting an example embodiment of a method of diminishing blisters in a metallic body.

FIG. 5 is a flow chart depicting an example embodiment of a method 500 in accordance with the process described with respect to FIGS. 4A-4G. At step 502, charged particle radiation is applied to a region of metallic body 102 (e.g., as described with respect to FIGS. 4A-4B). At step 504, additional charged particle radiation has been applied such that one or more blisters are formed and grow in size in the region (e.g., as described with respect to FIGS. 4C-4D). At step 506, still further charged particle radiation is applied such that a lithium compound layer is formed having sufficient size (e.g., thickness) to reach or become adjacent to (nearly reach) the one or more blisters. Reaching or nearly reaching the one or more blisters can allow the one or more blisters to diminish in size or be eliminated with further radiation. Step 506 can continue until blister size reduction substantially stops, until all blisters are eliminated, until a lithium compound layer of the desired size or thickness has been formed, or even longer depending on the application. The interval between steps 504 and 506, in some embodiments, may include a phase where blister formation in the region ceases or substantially ceases (or blister size growth in the region ceases or substantially ceases), but blister size reduction does not yet occur.

Figure 6A:
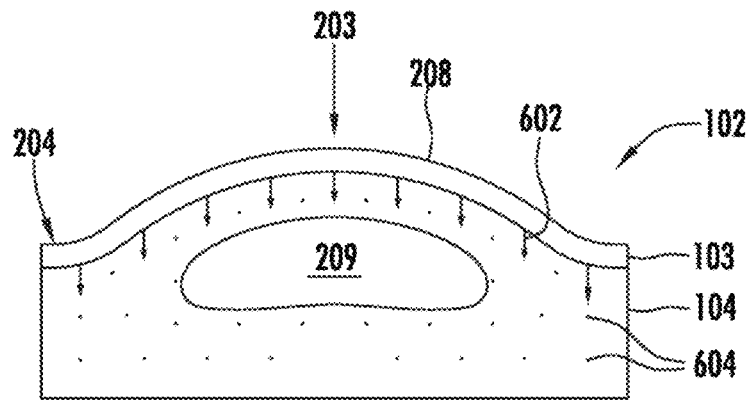
FIG. 6A is a cross-sectional view depicting an example embodiment with a partially formed amorphous region and a blister.
Figure 6B:
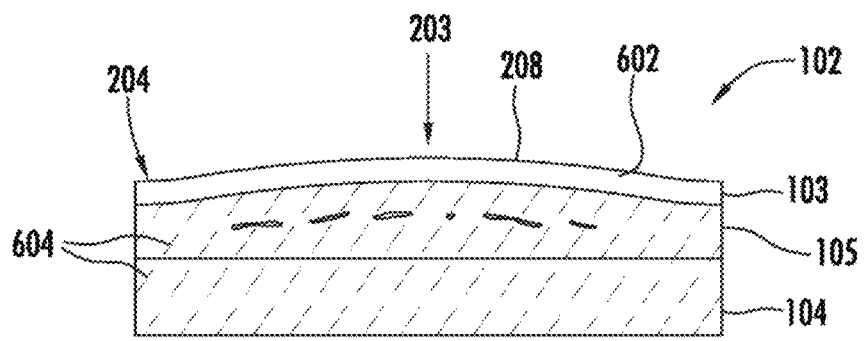
FIG. 6B is a cross-sectional view depicting an example embodiment of a metallic body with a substantially formed amorphous region and little to no blistering.

In certain embodiments the charged particle radiation can cause a partial or full transition of the substrate material from a crystalline (encompassing crystalline and polycrystalline) state to an amorphous state by breaking of the crystalline bonds. FIGS. 6A-6B are cross-sectional views similar to FIGS. 4E-4G depicting the formation of amorphous bulk material. In these embodiments the transition to amorphous material occurs during and after the formation of lithium compound, although formation of the amorphous material can occur independently from compound formation. In FIG. 6A charged particle radiation 203 results in the formation of a blister 208 with a gaseous pocket 209. Formation of a lithium compound layer occurs in the direction of arrows 602. Transition of the substrate material (e.g., copper) from a crystalline state to an amorphous state may partially occur as indicated by pattern 604. Continued exposure to radiation 203 causes compound layer 105 to thicken away from surface 204, and causes additional material transition to the amorphous state 604 in both the compound layer 105 and substrate region 104, particularly in the blister shell region between the gaseous pocket 209 and lithium layer 103. The transition to the amorphous state in these regions can be ull or partial (e.g., more than 50%, more than 75%, or more than 90%). In certain embodiments this transition to the amorphous state can be one of the causes, or the primary cause, for blister reduction or elimination. The amorphous transition can work in conjunction with the formation of compound layer 105 to cause blister reduction. Other mechanisms can contribute as well.

Figure 7:
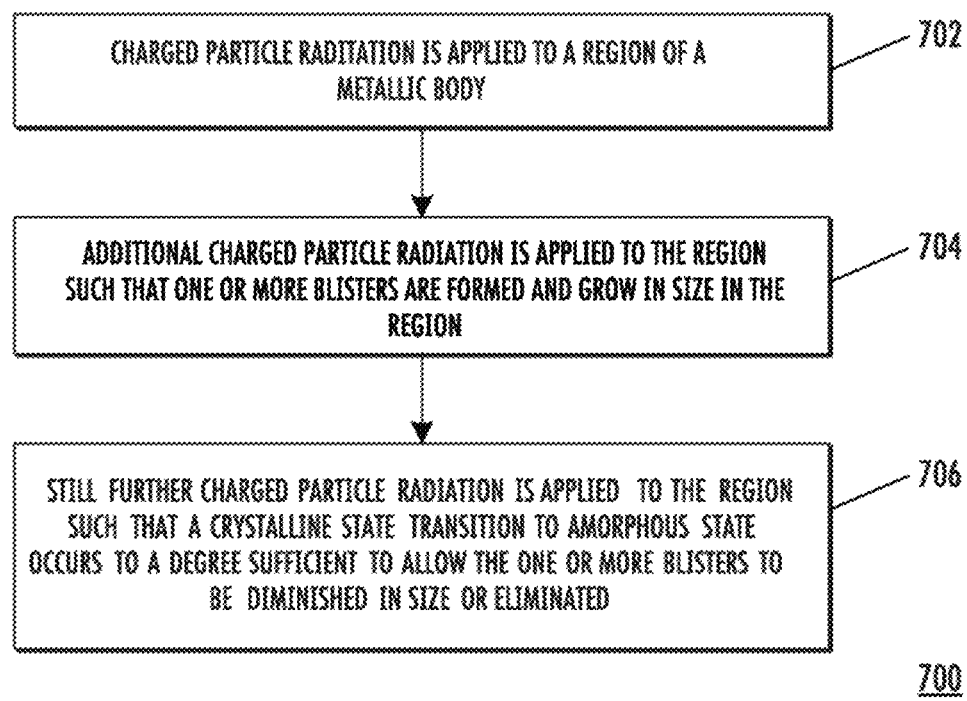
FIG. 7 is a flow chart depicting an example embodiment of a method of diminishing blisters in a metallic body.

FIG. 7 is a flow chart depicting an example embodiment of a method 700 in accordance with the process described with respect to FIGS. 6A-6B. At step 702, charged particle radiation is applied to a region of metallic body 102 (e.g., similar to FIGS. 4A-4B). At step 704, additional charged particle radiation has been applied such that one or more blisters are formed and grow in size, and a substrate region of the metallic body 102 may partly transition from a crystalline to an amorphous state (e.g., as described with respect to FIG. 6A). This can be accompanied by growth of a lithium compound layer and a partial transition of that compound from a crystalline to amorphous state. At step 706, still further charged particle radiation is applied such that the crystalline state transition to amorphous state continues to a degree sufficient to permit blister 208 to be reduced (e.g., 50%, 75%, 90%, or greater transition to amorphous state). This transition can occur throughout metallic body 102, but for purposes of blister reduction the transition occurs at least in the region of the substrate (and compound if present) between the blister and top surface 204 (the lithium layer need not transition). In some embodiments blister reduction may also be contingent upon enlargement of the compound layer to a depth that reaches or becomes adjacent to (nearly reaches) the one or more blisters. Step 706 can continue until blister size reduction substantially stops, until all blisters are eliminated, until a lithium compound layer of the desired size or thickness has been formed, or longer depending on the application. The interval between steps 704 and 706, in some embodiments, may include a phase where blister formation in the region ceases or substantially ceases (or blister size growth in the region ceases or substantially ceases), but blister size reduction does not yet occur.

The embodiments of metallic bodies 102 described herein can be subjected to methods 300, 500, or 700 during operation of the apparatus of which body 102 is a component or element, and thus can undergo blister resistance conditioning during operation itself. Alternatively (or additionally), embodiments of metallic bodies 102 can be subjected to method 300, 500, or 700 prior to operation, as a method of manufacturing or conditioning, and that conditioned material can then be assembled or installed as part of a larger system or apparatus or otherwise be first operated in a desired application with increased blister resistance.

In this and the other embodiments described herein, the charged particle radiation can be applied continuously or intermittently to achieve the blister reduction and/or resistance. For example, during a radiation application procedure the radiation can be applied (e.g., by a beam or reaction) in a continuous or pulsed manner (e.g., intermittent at a constant or variable frequency). This radiation application procedure can be stopped for a substantial period of time (e.g., such as when the system is powered down or otherwise brought off-line, e.g., for system maintenance, or otherwise) and then restarted, and anti-blister benefits can still be achieved even with this intermittent cycling of the overall system.

Metallic bodies 102 operating within or conditioned according to the processes described herein (with respect to FIGS. 2A-7 above and other embodiments to follow) can be used in numerous applications. For example, metallic bodies 102 can be used in plasma fusion devices, such as plasma-facing walls for containment chambers of fusion reactors. Metallic bodies 102 can also be used in particle accelerators, ion implantation devices, satellites and spacecraft, devices for isotope production, devices for hazardous materials detection, devices for assaying of precious metal ores, imaging devices, and others.

One example application of note is boron neutron capture therapy (BNCT), where a metallic body 102 can be configured for use as a target apparatus for generating neutrons in a neutron beam system. An example of a neutron beam system 800 is described in greater detail with respect to FIG. 8A herein.

BNCT is a form of radiation therapy for cancer treatment. In BNCT, a patient is dosed with a drug containing boron, where the drug has a property that causes the boron to be selectively absorbed by the cancer cells within any tumor sites in the patient's body. The patient is then exposed to neutron radiation, particularly epithermal neutrons with energies in the range of one kiloelectronvolt (keV) to 10 keV, and in some cases as high as 30 keV. These epithermal neutrons interact with the boron by a nuclear reaction that produces alpha particles having a very short range, e.g., on the order of the thickness of one cell. Thus, exposure of the boron containing cancer cells to epithermal neutrons generates alpha radiation in a dosage sufficient to kill the tumor cells without severe side effects to the surrounding tissue.

To generate sufficient flux of epithermal neutrons, a charged particle beam such as a proton (or positive hydrogen ion (H+)) beam is directed at a $^7$Li target, where the ensuing nuclear reaction p+$^7$Li→n+$^7$Be generates the neutron beam. $^7$Li is commonly considered the most optimal neutron producing target material for two reasons. First, it provides one of the highest conversion ratios of protons to neutrons. Second, p+$^7$Li is an endothermic reaction and requires the proton energy to be above a certain threshold, about 1.9 MeV, for neutron generation to occur. Neutrons generated at or above this threshold (e.g., from 1.9 MeV to about 3.0 MeV) have neutron energies of generally less than 1 MeV and can be slowed relatively easily to the epithermal range of about 1 keV-30 keV.

The neutrons can be slowed using a moderator. Slowing via the moderator nuclei occurs due to elastic and inelastic scattering, and this has a probabilistic character as neutron motion resembles Brownian particle motion. As a result, the lower the primary neutron energy is, the narrower the neutron energy spectrum. In this context, the $^7$Li(p,n)$^7$Be reaction, characterized by a rapid growth of the cross-section near the neutron generation threshold, seems to be ideal, as the amount of neutrons produced in the soft (e.g., <1 keV) and hard (>30 keV) energy ranges can be minimized. Clinicians generally want the amount of soft and hard neutrons to be minimized as they result in higher patient toxicity and more severe side effects. Thus, a neutron beam system operating in this range above the energy threshold of the $^7$Li reaction can be configured to strike an optimal balance between neutron yield and the quality of the resulting neutron energy spectrum.

Because the neutron generating reaction is endothermic, a significant amount of heat is generated, and the $^7$Li target (often referred to just as a lithium target) needs to account for this. Prior solutions place a lithium layer on a metallic substrate with a high thermal conductivity (e.g., copper) in combination with water cooling to keep the temperature of the target or target assembly low enough such that the lithium does not evaporate (e.g., and form radioactive contamination within the beamline). However these prior solutions have been susceptible to blistering as a result of the application of the energetic proton beam and much effort has been invested in preventing the formation of blisters in the lithium target.

Blister prevention techniques often involve placement of an anti-blistering material between the lithium and the underlying copper substrate. Materials with high hydrogen diffusion coefficients (e.g., tantalum, niobium, vanadium, and palladium) have been used, however these materials tend to have much lower thermal conductivity than copper and thus can make it more difficult to cool the target.

Generally, since lithium is characterized by high chemical activity, low melting point (e.g., 182° C.) and low thermal conductivity (e.g., 71 W/(m K) in the solid-state and 43 W/(m K) in the liquid state), designing a lithium neutron-generating target can be a difficult technical task. Other considerations should also be taken into account. For example, in addition to producing heat, neutron generation is accompanied by gamma ray flux. To significantly reduce the gamma ray flux and temperature on the lithium surface, the lithium layer should be thin enough such that protons are slowed down in it to the threshold of neutron generation. It is also desirable to use lithium having a relatively high purity to maximize the neutron yield. For example, relatively pure lithium provides a neutron yield that is approximately 1.43 times greater than lithium hydride, approximately two times greater than lithium oxide, and approximately 3.3 times greater than lithium fluoride. To prevent lithium evaporation, which may contaminate the beam system and facility with radioactive Be1 (captured inside of the lithium), the target should be intensively cooled. A thin underlying substrate should be used to permit the neutron moderator of the beam shaping assembly to be positioned as close as possible to the lithium layer. In some cases it is desirable that the target have an overall thickness that is less than a total projected range of the protons. Further, it is desirable that the substrate be resistant to radiation damage, easy to manufacture, and easy to remove from the system to facilitate disposal.

Figure 8A:
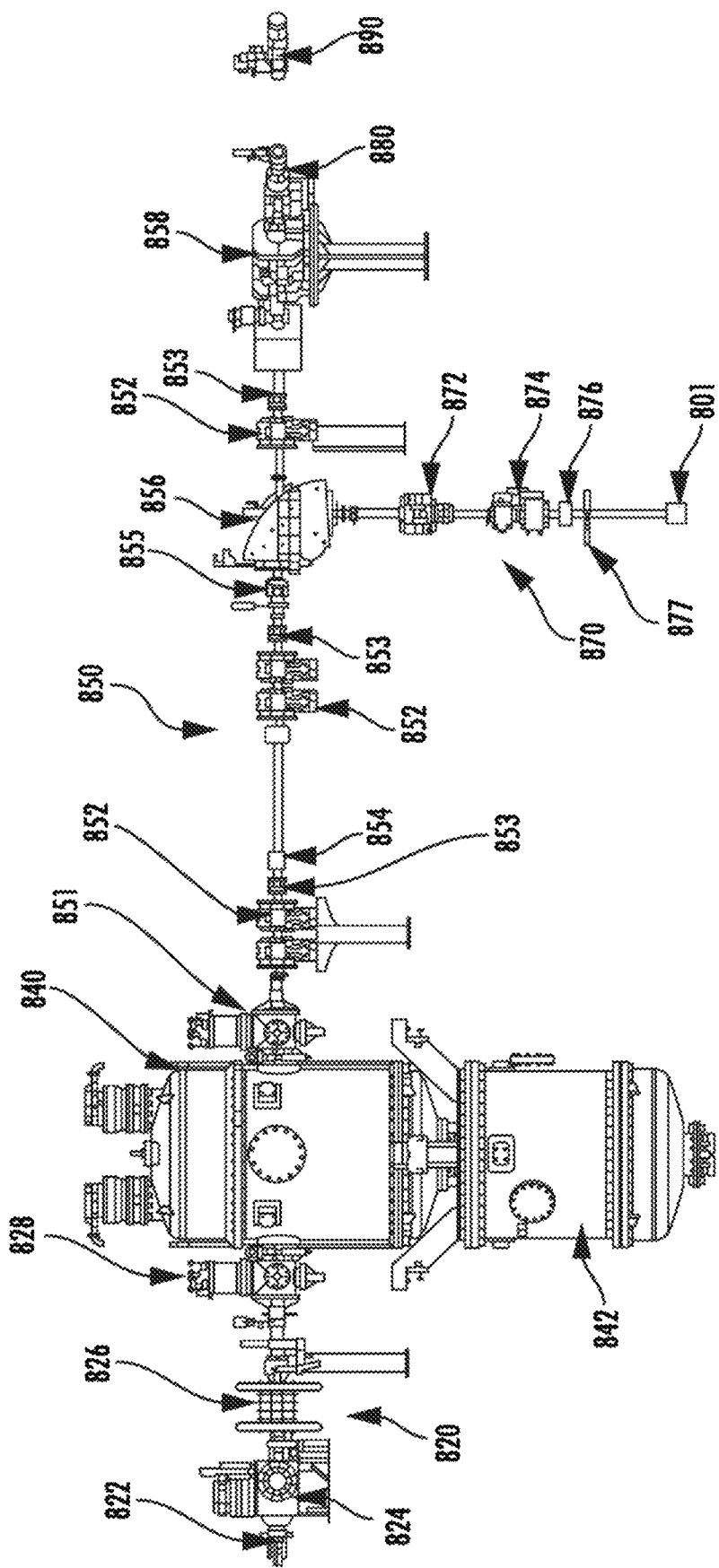
FIG. 8A is a schematic view depicting an example embodiment of an accelerator based neutron beam system.
Figure 8B:
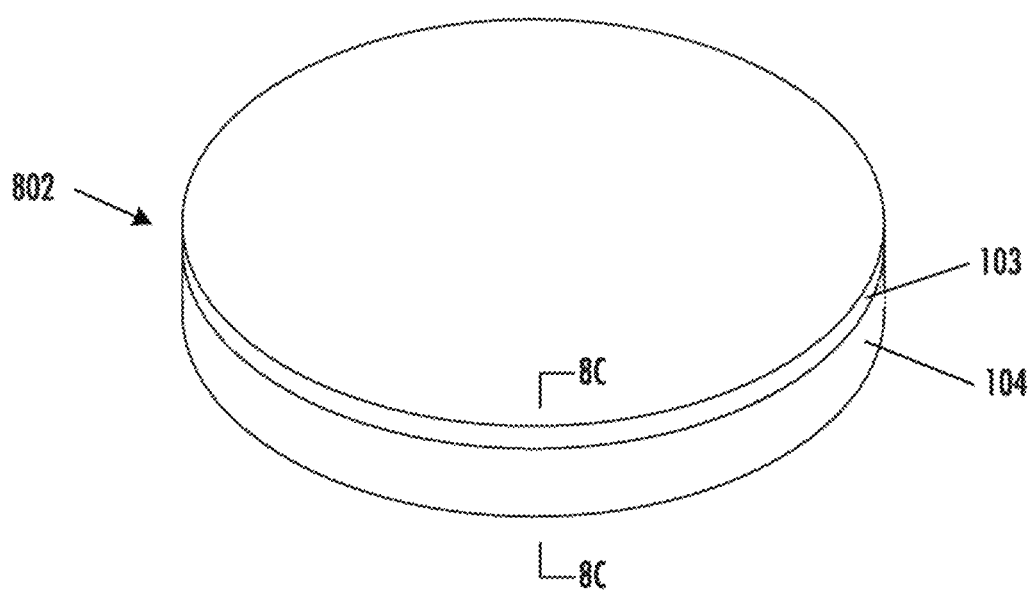
FIG. 8B is a perspective view depicting an example embodiment of target configured to generate neutrons.

FIG. 8A is a schematic view depicting an example embodiment of an accelerator based neutron beam system 800. While configurations of neutron beam systems vary, in this embodiment, system 800 includes a low energy beamline 820 that serves as an ion beam injector, a high voltage (HV) tandem accelerator 840 coupled to the ion beam injector 820, and a high-energy beamline 850 extending from the tandem accelerator 840 to lithium target assembly 801, which can house a lithium target 802 (see FIG. 8B). The ion beam injector 820 can include an ion source 822, an ion source vacuum box 824 extending from the ion source 822, a pre-accelerator tube 826 coupled to the ion source vacuum box 824, and a pumping chamber (e.g., with a built-in Faraday cup) 828 coupled between the pre-accelerator tube 826 and the tandem accelerator 840. Ion source 822 serves as a source of charged particles (which in example embodiments are negative hydrogen ions) which can be accelerated, conditioned and eventually used to produce neutrons when delivered to lithium target 802.

Two types of negative ion sources 822 that differ by the mechanism of generation of negative ions are: the surface type and volume type. The surface type requires presence of cesium (Cs) on the specific internal surfaces. A discussion of a surface type negative ion source is provided in published PCT Application No. WO2014039579A2, which is incorporated herein by reference in its entirety for all purposes. The volume type relies on formation of negative ions in the volume of a high current discharge plasma. Both types of ion sources can deliver sufficient negative ion current.

The ion source vacuum box 824, pre-accelerator tube 826 and pumping chamber 828 are configured to transfer the ion beam from the ion source 822 to the input of the tandem accelerator 840. This low energy beamline 820 may have one or more magnetic elements to focus and steer the beam to match the beam to the beamline axis and the acceptance angle of the tandem accelerator 840.

Pre-accelerator tube 826 provides acceleration of the negative ion beam injected from ion source 822. Pre-accelerator tube 826 serves an important function of beam focusing to achieve overall convergence to match aperture area at high voltage tandem accelerator 840 entrance.

Tandem accelerator 840, which is powered by a high voltage power supply 842 coupled thereto, can produce a proton beam with an energy equal to twice the voltage applied to the accelerating electrodes positioned within the tandem accelerator 840. The energy level of the proton beam is achieved by accelerating the beam of negative hydrogen ions from the input of the tandem accelerator 840 to the innermost high-potential electrode, stripping two electrons from each ion, and then accelerating the resulting protons (H+ ions) downstream by the same applied voltage.

The high-energy beamline 850 transfers the proton beam from the output of the tandem accelerator 840 to target 802 in target assembly 801 positioned at the end of a branch 870 of the beamline extending into a patient treatment room. In the example embodiment shown in FIG. 8A, high-energy beamline 850 includes three branches 870, 880 and 890 to extend into three different patient treatment rooms. High-energy beamline 850 can include a pumping chamber 851, quadrupole magnets 852 and 872 to prevent de-focusing of the beam, dipole or bending magnets 856 and 858 to steer the beam into treatment rooms, beam correctors 853, diagnostics such as current monitors 854 and 876, fast beam position monitor 855 section, and a scanning magnet 874.

The configurations of high-energy beamline 850 depends on the configuration of the treatment facility. The embodiment of FIG. 8A is for a two-story configuration of the treatment facility. One of the treatment rooms, which is closer to target assembly 801, is located on the lower story. The beam is delivered to target assembly 801 with the use of bending magnet 856. After that, quadrupole magnets 872 focus the beam to the certain size at target 802. The beam can be moved (e.g., rastered, scanned, or oscillated) across the surface of target 802 by magnets 874. The beam movement can help to achieve smooth and even time-averaged distribution of the proton beam on lithium target 802, preventing overheating and making neutron generation more uniform within the lithium layer of target 802.

After traversing scanning magnets 874, the beam is delivered into a current monitor 876, which measures beam current, and can act as a safety interlock. Target assembly 801 can be physically separated from the high energy beamline volume with a gate valve 877. A function of the gate valve is separating of the vacuum volume of the beamline from the target while target exchange/loading. The horizontal orientation of the beamline (second and possibly third treatment rooms off branches 880 and 890) is shown (partially) on FIG. 8A as well. In this case the beam is not bent by 90 degrees by a bending magnet 856, but rather goes straight to the right, then it passes quadrupole magnets 852, which are located in the horizontal beamline. After, the beam could be bent by another bending magnet 858 to a needed angle, depending on the room configuration. Otherwise, the bending magnet 858 could be replaced with a Y-shaped magnet in order to split the beamline into two directions for two different treatment rooms located on the same floor. Impingement of the beam on target 802 produces the neutron beam, which can then be shaped and modified by a neutron beam shaping assembly (not shown), that can output the neutron beam directly to the patient.

Figure 8C:
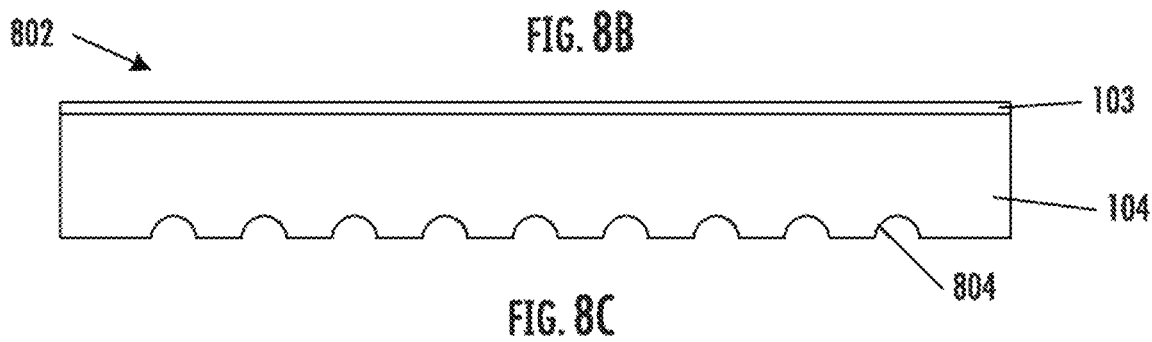
FIG. 8C is a cross-sectional view of the embodiment taken along line 8C-8C of FIG. 8B.
Figure 8D:
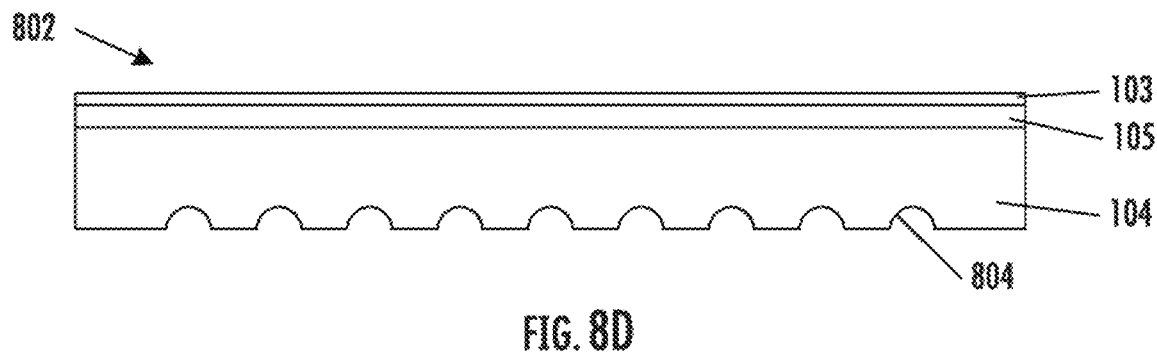
FIG. 8D is another cross-sectional view of the embodiment having a lithium compound layer.
Figure 8E:
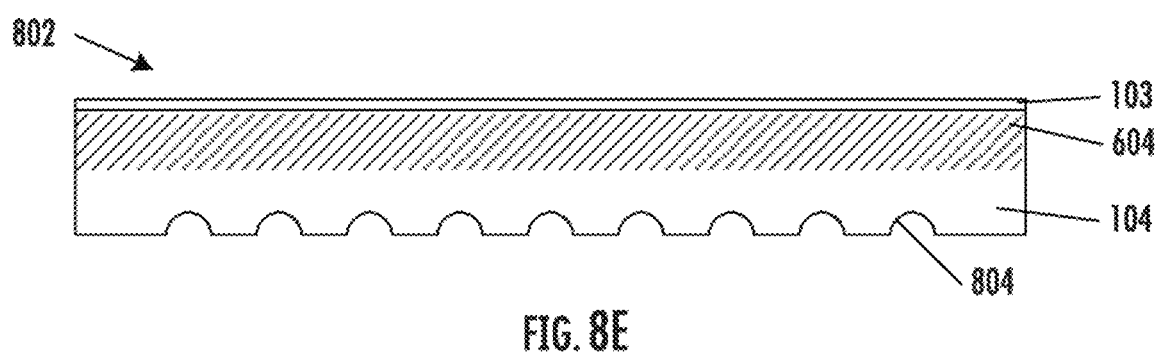
FIG. 8E is another cross-sectional view of the embodiment having an amorphous region.
Figure 8F:
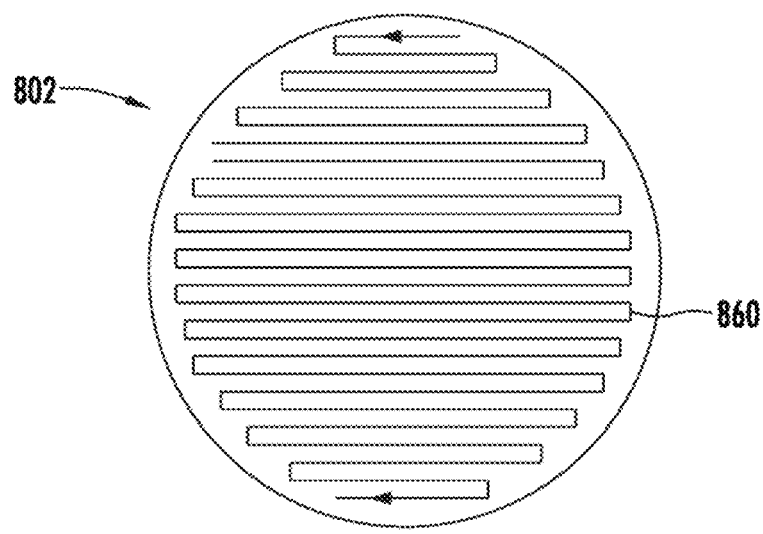
FIGS. 8F and 8G are frontal views of an example embodiment of a target showing a stepped pattern and spiral pattern of beam movement, respectively.
Figure 9A:
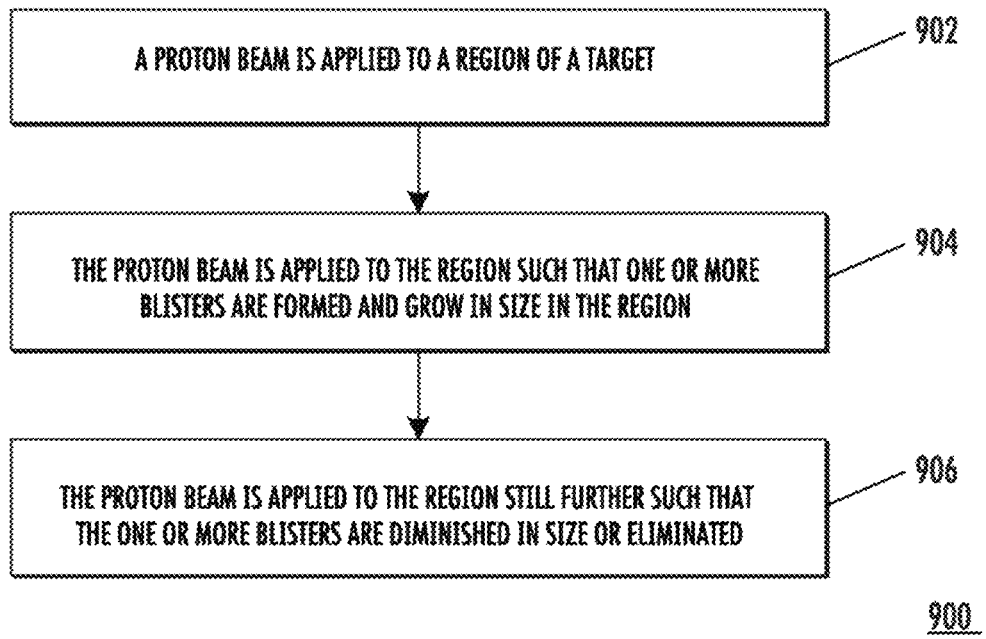
FIGS. 9A, 9B, and 9C are flow diagrams depicting example embodiments of methods of producing a neutron beam with a target with anti-deformation benefits.

FIG. 9A is a flow diagram depicting an example embodiment of a method 900 of producing a neutron beam similar to the process described with respect to FIG. 3. At step 902, a proton beam is applied to a region of target 802 (e.g., as described with respect to FIGS. 2A-2B). The proton beam preferably has an energy in the range of 1.9 MeV to 3.0 MeV, although it is not limited to such. The proton beam can be applied in a continuous or pulsed manner, can be held in a static position, or can be moved across the surface of target 802 in any desired pattern (e.g., see FIGS. 8E and 8F showing stepped and spiral patterns, respectively). At step 904, the proton beam is applied such that one or more blisters are formed and grow size in the region (e.g., as described with respect to FIGS. 2C-2D). This can occur without significant degradation in the neutron yield as will be described with respect to FIGS. 10B-10C. At step 906, the proton beam is applied still further such that the one or more blisters are diminished in size. Step 906 can continue until blister size reduction substantially stops, until all blisters are eliminated, or thereafter to continue neutron production for BNCT. Again, proton irradiation can continue without significant degradation in the neutron yield so long as, for example, the lithium layer does not become overly thinned. The interval between steps 904 and 906, in some embodiments, may include a phase where blister formation in the region ceases or substantially ceases (or blister size growth in the region ceases or substantially ceases), but blister size reduction does not yet occur.

Figure 9B:
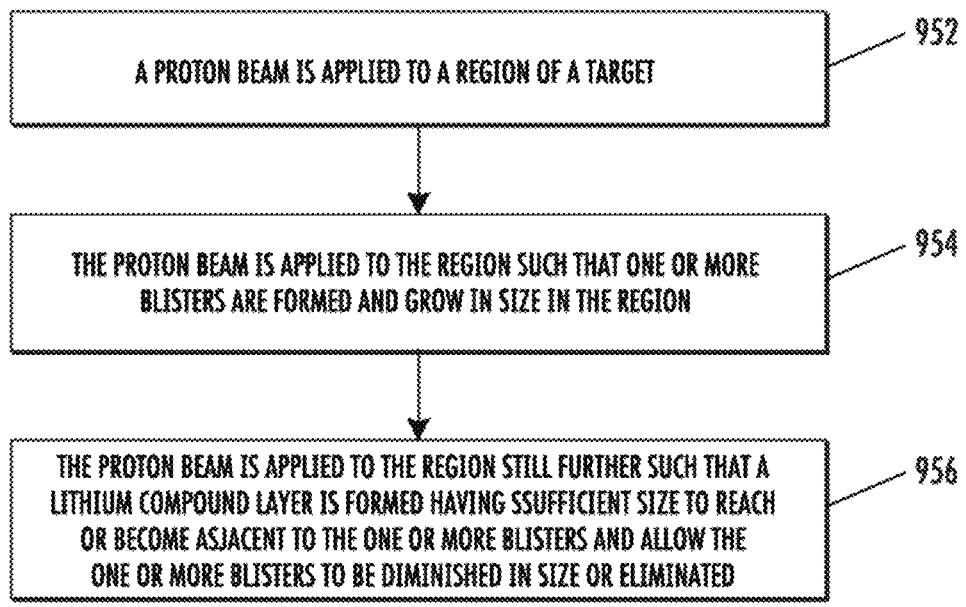

FIG. 9B is a flow diagram depicting an example embodiment of a method 950 of producing a neutron beam similar to the process described with respect to FIG. 5. At step 952, a proton beam is applied to a region of target 802 (e.g., as described with respect to FIGS. 4A-4B). Like with the proceeding embodiment, the proton beam preferably has an energy in the range of 1.9 MeV to 3.0 MeV, although it is not limited to such. The proton beam can again be applied in a continuous or pulsed manner, can be held in a static position, or can be moved across the surface of target 802 in any desired pattern. At step 954, the proton beam is applied such that one or more blisters are formed and grow size in the region (e.g., as described with respect to FIGS. 4C-4D). This can occur without significant degradation in the neutron yield as will be described with respect to FIGS. 10B-10C. At step 956, the proton beam is applied still further such that a lithium compound layer is formed having sufficient size (e.g., thickness) to reach or become adjacent to (nearly reach) the one or more blisters, and allow the one or more blisters to diminish in size with further radiation. Step 956 can continue until blister size reduction substantially stops, until all blisters are eliminated, until a lithium compound layer of the desired size or thickness has been formed, or thereafter to continue neutron production for BNCT. Again, proton irradiation can continue without significant degradation in the neutron yield so long as, for example, the lithium layer does not become overly thinned through formation of the compound layer. The interval between steps 954 and 956, in some embodiments, may include a phase where blister formation in the region ceases or substantially ceases (or blister size growth in the region ceases or substantially ceases), but blister size reduction does not yet occur.

Figure 9C:
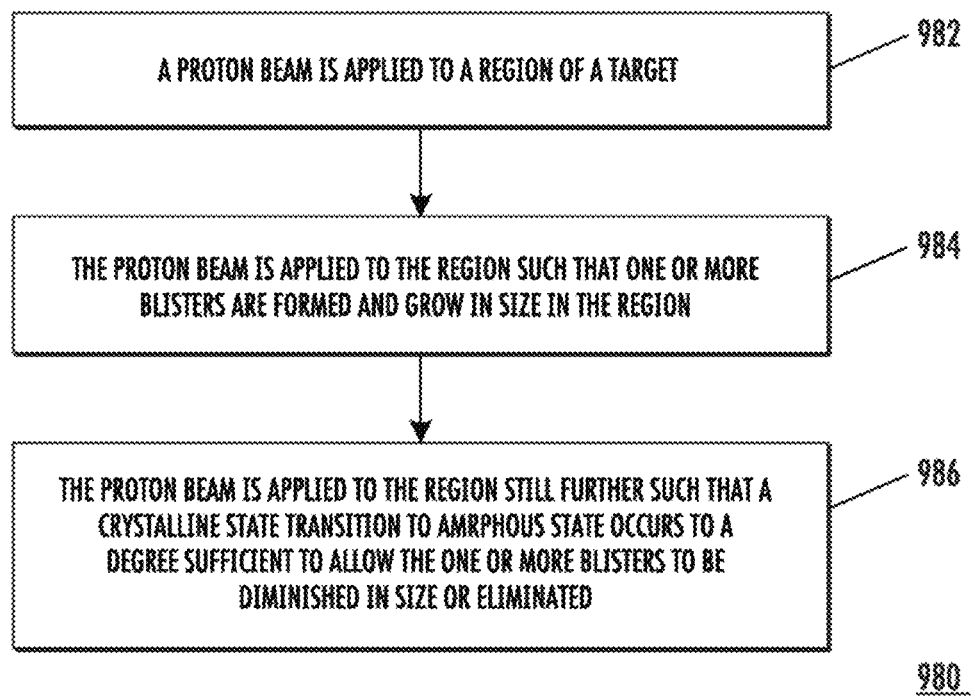

FIG. 9C is a flow diagram depicting an example embodiment of a method 980 of producing a neutron beam similar to the process described with respect to FIG. 7. At step 982, a proton beam is applied to a region of target 802. The proton beam preferably has an energy in the range of 1.9 MeV to 3.0 MeV, although it is not limited to such. The proton beam can again be applied in a continuous or pulsed manner, can be held in a static position, or can be moved across the surface of target 802 in any desired pattern. At step 984, the proton beam is applied such that one or more blisters are formed and grow size, and a substrate region of target 802 partly transitions from a crystalline to an amorphous state (e.g., as described with respect to FIG. 6A). This can be accompanied by growth of a lithium compound layer and a partial transition of that compound from a crystalline to amorphous state. This can occur without significant degradation in the neutron yield as will be described with respect to FIGS. 10B-10C. At step 986, still further charged particle radiation is applied such that the transition to amorphous state continues to a degree sufficient to permit blistering to be reduced (e.g., 50%, 75%, 90%, or greater transition to amorphous state). This transition can occur throughout target 802, but for purposes of blister reduction the transition occurs at least in the region of the target 802 between the blister and top surface 204 (the lithium layer need not transition). Step 986 can continue until blister size reduction substantially stops, until all blisters are eliminated, until a lithium compound layer of the desired size or thickness has been formed, or thereafter to continue neutron production for BNCT. In some embodiments blister reduction may also be contingent upon enlargement of the compound layer to a depth that reaches or becomes adjacent to (nearly reaches) the one or more blisters. Step 986 can continue until blister size reduction substantially stops, until all blisters are eliminated, until a lithium compound layer of the desired size or thickness has been formed, or longer depending on the application. Again, proton irradiation can continue without significant degradation in the neutron yield so long as, for example, the lithium layer does not become overly thinned through formation of the compound layer. The interval between steps 984 and 986, in some embodiments, may include a phase where blister formation in the region ceases or substantially ceases (or blister size growth in the region ceases or substantially ceases), but blister size reduction does not yet occur.

The embodiments of targets 802 described herein can be subjected to methods 900, 950, or 980 during operation of neutron beam system 800. This system operation can be for the purpose of conditioning target 802 in order to enhance its blister resistance when used on a patient. Alternatively, this system operation can be while the patient is treated, such that blisters are formed and reduced in size during one or more procedures that apply neutrons directly to a patient for treatment purposes. Implementation of methods 900, 950, or 980 can also occur by operation of system 800 during a combination of both non-patient and patient use. In another embodiment, methods 900, 950, and/or 980 can be implemented during manufacture of target 802 (e.g., prior to distribution of target 802 to a BNCT patient center) using radiation produced by a charged particle radiation system other than that designed for use on human patients.

Referring back to FIG. 8B, this figure is a perspective view depicting an example embodiment of target 802 prior to being subjected to particle radiation sufficient to induce blistering. In this embodiment, target 802 is disk shaped and similar to metallic body 102 in that it includes lithium layer 103 and metallic substrate 104. Copper has been shown to be particularly advantageous as a material for substrate 104 although the embodiments herein are not limited to such. FIG. 8C is a cross-sectional view of target 802 taken along line 8C-8C of FIG. 8B. FIG. 8C depicts the presence of cooling channels 804 in the backside of substrate 104. Channels 804 can be used to circulate coolant across the backside of substrate 104 during operation of system 800, in order to dissipate heat produced by the endothermic neutron generating reaction. FIG. 8D is a cross-sectional view of target 802 after being subjected to particle radiation sufficient to form lithium compound layer 105. In embodiments where substrate 104 is copper, the lithium compound layer 105 is a lithium copper compound. FIG. 8E is a cross-sectional view of target 802 after being subjected to particle radiation sufficient to form amorphous region 604 in substrate 104.

Figure 8G:
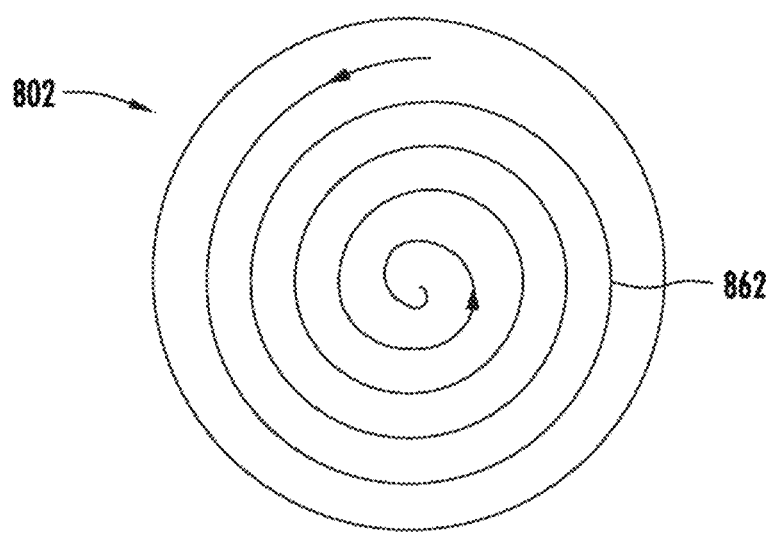

FIGS. 8F and 8G are frontal views of target 802 showing a stepped pattern 860 and spiral pattern 862 of beam movement, respectively. The beam can be moved continually back and forth along these patterns in both directions (one direction indicated in the figures). Depending on the beam spot size, the pattern may or may not result in uniform fluence delivered across the entire surface of target 802. The anti-deformation benefits described herein can be realized with both uniform and non-uniform fluence across the surface of target 802 depicted here. In these embodiments, the lithium layer is present across the entire surface shown here, however in other embodiments of target 802, the lithium layer may be confined to only an inner region of the surface shown here.

Lithium layer 103 can be in either a solid form or liquid form. If in liquid form, lithium layer 103 can be placed over substrate 104 in solid form such that the solid substrate can be oriented at a desired angle (e.g., 0-90 degrees) with respect to the incoming beam axis. The liquid lithium should is formed over the substrate in a manner that does not permit significant amounts of lithium to evaporate (and thereby potentially contaminate the system or facility). A liquid lithium layer enables utilization of substantially higher power densities of the proton beam, which in turn enables use of a relatively smaller target diameter or width.

Lithium layer 103 can have a thickness that is preferably sufficient to enable growth of the lithium compound layer while maintaining constant neutron yield, as diffusion of the lithium into the substrate will cause lithium layer 103 to thin. Table 2 lists example lithium characteristics for different proton energies in natural abundant lithium (e.g., 7Li containing about 10% 6Li). The projected range in lithium is the range for the proton at each energy to stop motion. The depth to threshold is the depth within lithium that the proton reaches approximately 1.88 MeV, which is the threshold at which neutron generation ceases. For pure 7Li, the depth to threshold is slightly higher (e.g., 17.7 microns for 2.00 MeV, 92.5 microns for 2.50 MeV).

TABLE 2

| Proton Energy (MeV) | Projected Range in Lithium (microns) | Depth to Threshold (microns) |
| --- | --- | --- |
| 3.00 | 319.77 | 176.27 |
| 2.75 | 274.89 | 131.39 |
| 2.50 | 233.11 | 89.61 |
| 2.25 | 194.48 | 50.98 |
| 2.00 | 159.08 | 15.58 |
| 1.80 | 133.12 | NA |

A lithium layer used in a neutron generating target preferably has a thickness of at least the depth to threshold value, and thus the desired thickness of the lithium layer is dependent on the expected energy of the incident protons. Generally, the lithium layer thickness for a BNCT application can be in the range of 1-300 microns to accommodate proton energies in the 1.88-3.0 MeV range.

Figure 10A:
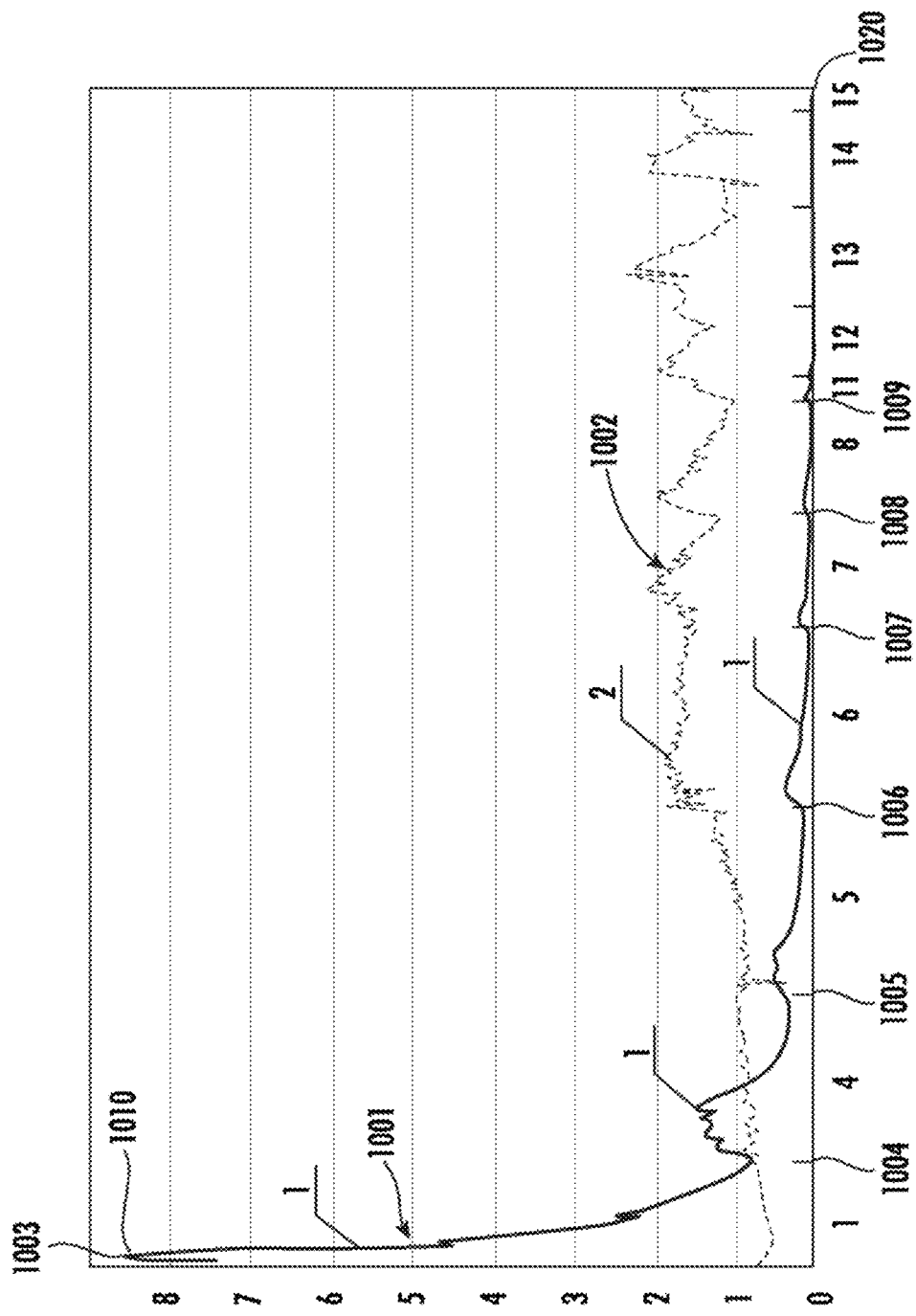
FIGS. 10A, 10B, and 10C are graphs depicting data collected during experimental verification of the embodiments described herein.
Figure 10B:
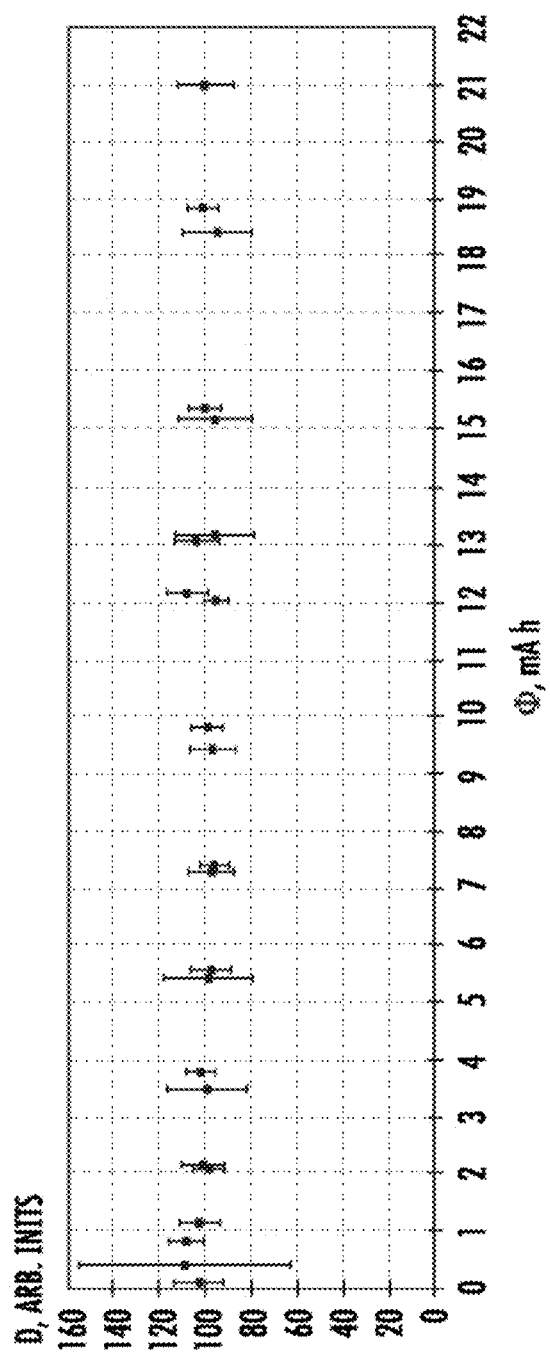
Figure 10C:
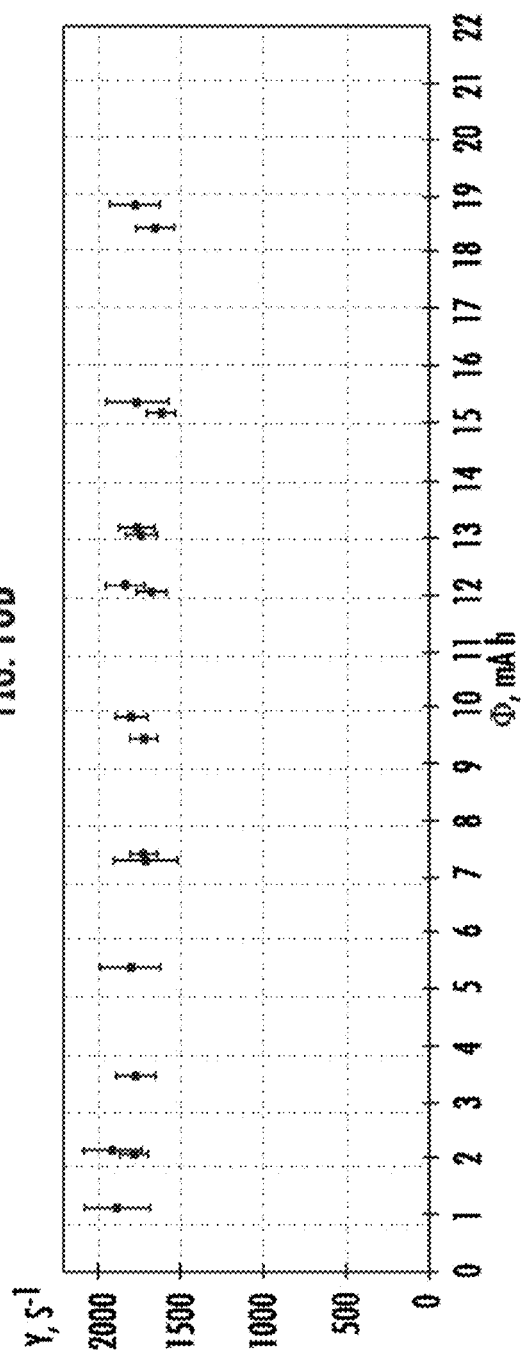

FIGS. 10A-10C are graphs depicting data collected during experimental verification of the embodiments described herein. This experimental data reflects results collected after exposing an embodiment of a target 802 with proton radiation in the form of the beam generated by an embodiment of a neutron beam system 800 similar to that described with respect to FIGS. 8A-8C. The target under study included a substrate 104 of 99.996% fine-grained copper with a lithium layer 103 having an 84 μm (micron) thickness that was evaporated onto substrate 104. The target was irradiated by a proton beam having a diameter of approximately 10 mm and a current of 500±10 μA for 11 days (4 hours (h) per day) over a 15 day span. The integral of current on the sample was 21.08 mA h. The target was mainly irradiated while the beam had a proton energy of 1.8 MeV, below the neutron generation threshold, and for a short time at larger energies of 1.92 and 2.04 MeV to determine the neutron yield (see FIGS. 10B-10C).

Figure 11A:
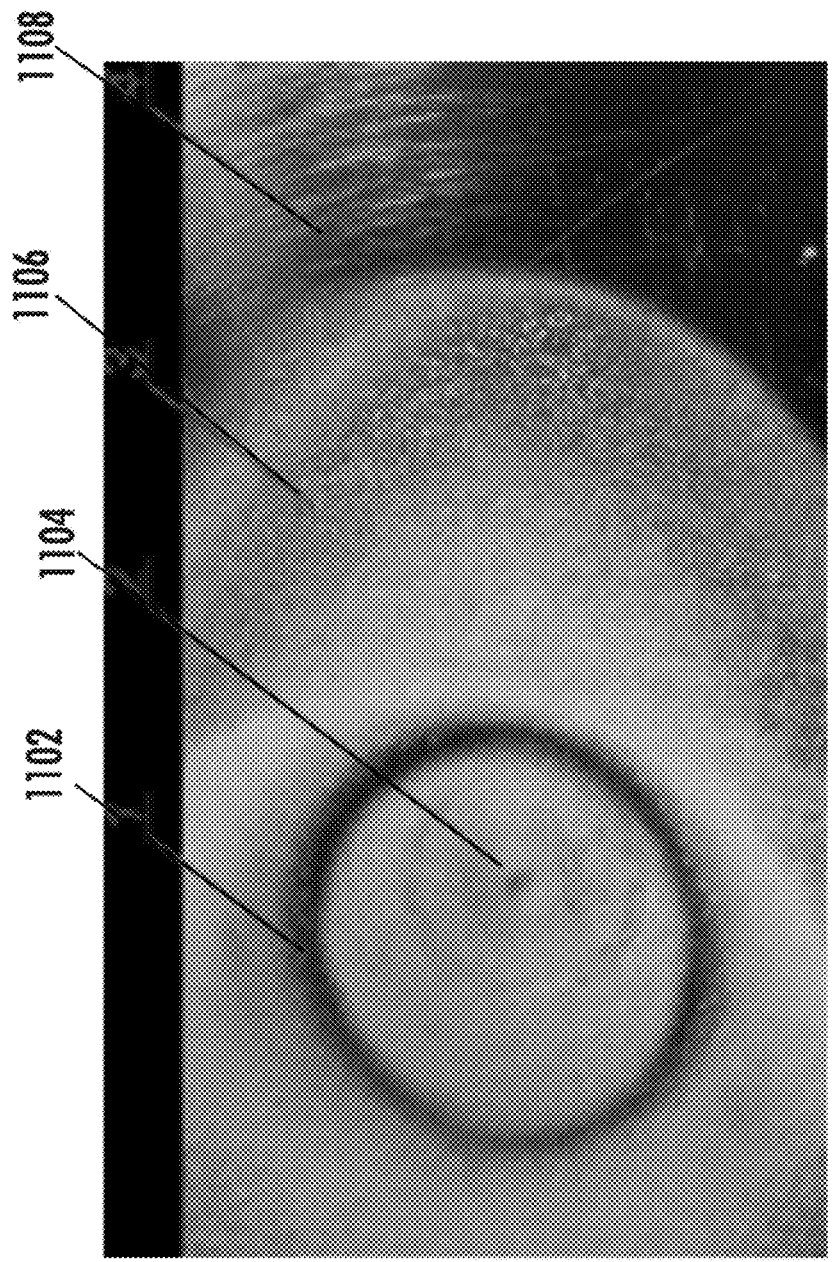
FIGS. 11A, 11B, and 11C are images of regions of a target after exposure to a proton beam.
Figure 11B:
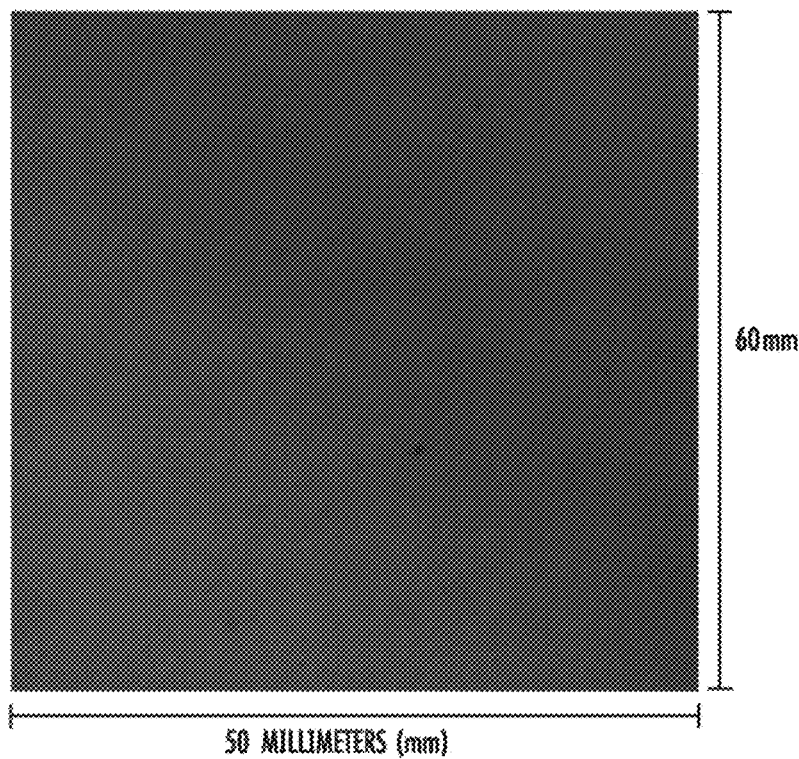
Figure 11C:
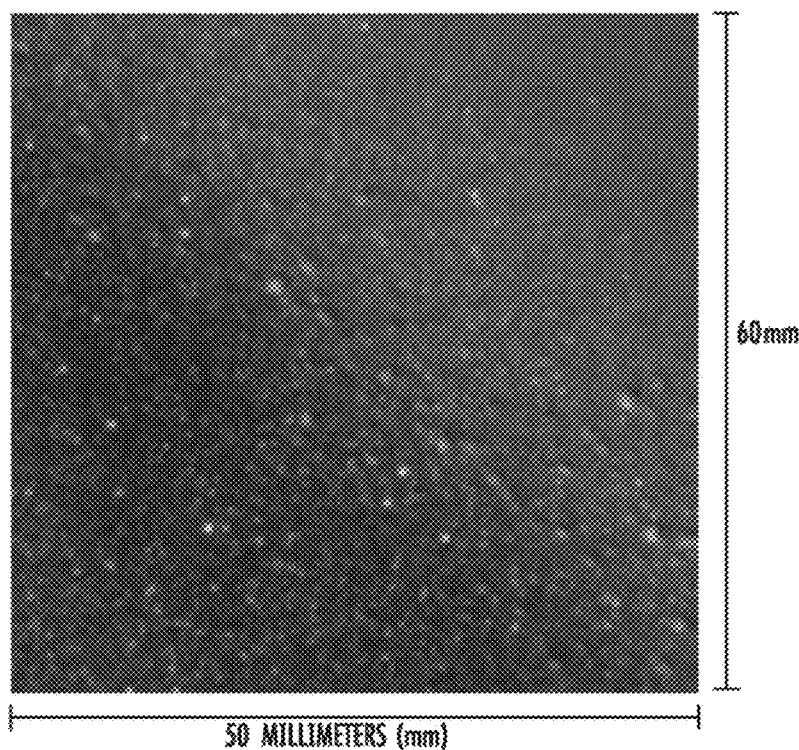

FIG. 10A is a graph depicting the relative number of blisters (y-axis) (relative number in the center of the beam) versus irradiation time (x-axis), which is time that the beam was applied to target 602. During the entire irradiation time the surface of the sample being studied was monitored by a KX InfiniMax™ long-distance microscope with a Basler Ace acA4112-30uc CMOS camera and a Hikvision video camera, and the video signals were recorded. The appearance and disappearance of blisters were clearly observed in different parts of the target surface. FIG. 11A is a macroscopic image of the lithium surface, and FIGS. 11B-11C are images taken by the long-distance microscope on the sixth day of irradiation. FIG. 11A shows a dark band 1102 with a band width of approximately 1 mm and an inner diameter of approximately 13 mm that coincides with the position of the main power of the proton beam. Region 1104 corresponds to the center of the target 802. Region 1106 corresponds to a periphery region outside of the main beam area 1102 that was still exposed to proton radiation. Region 1108 indicates the target surface not irradiated by protons. FIG. 11B is a close up showing the region 1102 of the lithium target surface corresponding to incidence by the center of the proton beam and FIG. 11C shows a close up of region 1106 of the lithium target surface on the periphery of the beam. It is seen that the lithium surface is homogeneous in the center of the proton beam, with blisters being absent, while blisters are distinct at the periphery of the beam.

The lithium surface modification by blisters was quantitatively determined as high brightness regions in the chosen part of the image. Every 720th frame of the video signal file was processed with a computer (approximately every 30 seconds). The processing distinguished high brightness regions corresponding to blisters and determined the areas of these regions in two parts of the image: in the center of the beam and on its periphery. The result of processing of the microscope video signal is illustrated in FIG. 10A, with curve 1001 corresponding to the region of the target surface impacted by the center of the beam, and curve 1002 corresponding to the region of the target surface impacted by the periphery of the beam. Here, the Y axis is an relative quantity of high brightness areas of the chosen part of the image (in the center of the beam and on the periphery) and the X axis shows the sequence of the processed image frames grouped by days of irradiation for 11 different days in a 15 day span. A majority of the portion of curve 1001 indicating the rise of blisters from time zero to the peak value 1010 is omitted. To make the result visible, vertical lines separating one day of irradiation from another are drawn in the plot. Because the output of the beam was not varied while in operation, the x-axis also generally corresponds to the proton fluence upon target 802. The total time indicated by 1020 is approximately 42 hours.

The blister count data 1001 demonstrates that at time 1003, blister formation had occurred in target 802 and had reached a peak level 1010. From time 1003 until time 1004 the blister count in target 802 rapidly decreased. As described with respect to the embodiments of FIGS. 4A-5, at time 1003 a lithium compound layer that had been forming between lithium layer 103 and substrate 104 may have reached a sufficient depth to allow hydrogen to diffuse from the blisters and out of body 102. Alternatively, as described with respect to the embodiments of FIGS. 6A-7, a transition from crystalline to amorphous structure may have occurred in the material forming the blister, such as the blister shell, and then this shell together with penetrated lithium removed into the substrate at large. Alternatively a combination of both may have occurred.

The following embodiments describe still further mechanisms that may have contributed in whole or in part to reduction of blister size and/or quantity. For example, proton beam exposure may cause convective forces to reduce the blisters, such as by turning lithium from solid to localized liquid form (e.g., a hotspot) which can allow the hydrogen to escape and/or cause the blister shell to be removed into the substrate. By way of another example, proton beam exposure may cause a capillary system of capillary forces to reduce the blisters, such as by causing lithium to penetrate into the crack, crevices, or other deformations in the substrate material, thereby allowing the hydrogen to escape and/or cause the blister shell to be removed into the substrate. A combination of convective and capillary action may also be the mechanism.

In the experiment, at time 1004 beam application was stopped for a period of time and then subsequently restarted. As result of this stoppage, upon restarting there was a brief period of blister formation from time 1004 to time 1005, at which point blister reduction commenced again and the total number of blisters dropped to a still lower level than was present at time 1004. Similar cycles occurred at times 1006, 1007, 1008, and 1009. However, the target 602 exhibited increased resistance to blister formation at the outset of each cycle such that the overall trend exhibits blister reduction an increased resistance to blister formation over time. The total number of blisters dropped to a count of near zero at the end of the experiment, which is a reduction greater than 99% of the peak. In other embodiments the reduction may be somewhat less, e.g., greater than 75%, greater than 90%, or greater than 95%.

FIGS. 10B and 10C are graphs depicting neutron yield from target 602 on the y-axis versus proton current integral $\Phi$ in milliamp hours (mAh) on the x-axis. The data in FIG. 10B was measured by a dosimeter and displays neutron dose rate D on the y-axis. The data in FIG. 10C was measured by a neutron detector and shows count rate Y in inverse seconds on the y-axis. In these graphs, point 21 on the x axes corresponds to a proton fluence of $6.3 \pm 0.6 \times 10^{20}$ protons per square centimeter ($p/cm^{-2}$). Both graphs indicate that neutron yield remained generally constant as proton fluence increased, and the neutron yields were generally in the range of from 95 to 108 for the dosimeter of FIG. 10B and from 1617 to 1915 for the detector of FIG. 10C. Point 21 also generally corresponds to point 1020 on FIG. 10A. Thus, the neutron yield remained generally constant across those time periods when blisters were been formed and when blisters were been reduced and eliminated. Thus the neutron yield was generally unaffected by the presence of blisters. The lack of degradation in the neutron yield also indicates that hydrogen diffusing from the substrate 104 through lithium layer 103 did not form hydrides or hydroxides with the lithium or lithium copper (or formed only a trace or negligible amount so as to not substantially degrade the neutron yield while the blisters were formed and eliminated). The proton fluence of point 21 can be expressed in terms of patient treatment. If that fluence is scaled to, for example, a target having an exposure region of roughly 10 cm in diameter, being used with a proton beam having an energy of 2.3 MeV and a current of 10 milliamps (mA), then the fluence of point 21 would correspond to BNCT therapy for approximately 340 patients (assuming 40 minutes per patient).

In some of the preceding embodiments, techniques are described where application of charged particle radiation to metallic body causes that body to undergo a first phase of blister formation filed by a second phase where the blisters are diminished in size or eliminated altogether without requiring formation of a lithium compound layer. Also described herein are embodiments where were the first phase of blister formation is followed by the second phase of blister reduction or elimination by way of the formation of the lithium compound layer. Still further, embodiments are described herein where were the first phase of blister formation is followed by the second phase of blister reduction or elimination by way of transition of the substrate material, alone or in combination with a lithium compound, from a crystalline state to a mostly amorphous state. In addition to these aforementioned embodiments, additional embodiments will now be described where the lithium compound layer and/or amorphous material are formed prior to the radiation exposure that would typically result in blister formation. These embodiments with the pre-existing lithium compound layer and/or amorphous structure have increased resistance to blister formation and can prevent blister formation altogether under certain conditions, thus avoiding any residual, and potentially undesirable, structural deformations that may persist even after the blisters have been reduced and/or eliminated.

The embodiment of metallic body 102 described with respect to FIGS. 1D-1E can be fabricated prior to exposure to charged particle radiation such that blisters are formed.

For example, lithium compound layer 105 can first be formed on or in, deposited on, or coupled to metallic substrate 104, and then lithium layer 103 can be subsequently formed on or in, deposited on, or coupled to lithium compound layer 105. Conversely, lithium compound layer 105 can first be formed on or in, deposited on, or coupled to lithium layer 103, and then metallic substrate 104 can be subsequently formed on, deposited on, or coupled to lithium compound layer 105.

In another embodiment, metallic body 102 is first fabricated with lithium layer 103 in direct contact with substrate 104. Metallic body 102 can then be subjected to one or more stimuli, e.g., heat, electricity, and/or pressure for a particular time, such that the lithium of layer 103 diffuses into substrate 104 and forms compound layer 105 in a region previously occupied by just the lithium layer, just the metallic substrate, or both. The conditions and time that the one or more stimuli are applied can determine the resulting thickness 112 of compound layer 105.

Substrate 104 having an amorphous structure can be provided with a lithium layer 103 thereon, or can be transitioned to the amorphous structure after the addition of lithium layer 103. Similarly, lithium compound layer 105 having an amorphous structure can also be provided according to the techniques described above, or can be provided in a crystalline state and then transitioned to an amorphous state. The metallic body 102 can then be used in the desired application with the pre-existing amorphous structure.

The thickness 112 of compound layer 105 and/or the amorphous portion of body 102 may be selected to mitigate blister formation based on the expected conditions and nature of the radiation to which body 102 will be exposed. For example, it may be desirable to form compound layer 105 to a depth from surface 204 that reaches the location where blister formation would otherwise occur under the expected radiation conditions. The depth of blister formation can be dependent on factors such as the type of radiation (e.g., proton, ion), energy of the radiation, purity of substrate 104, type of substrate metal, and others.

Embodiments of metallic body 102 with the pre-existing lithium compound layer and/or pre-existing mostly amorphous structure can then be used in the desired application without the formation of blisters, or substantially without the formation of blisters. For example, in a BNCT application where a lithium target 602 has a pre-existing lithium compound layer (similar to FIG. 8D) and/or a pre-existing amorphous structure (similar to FIG. 8E), a proton beam having an energy in the range of 1.9 MeV-3.0 MeV (more preferably in the range of 2.3 MeV-2.6 MeV) and a current in the range of 1-20 mA (more preferably in the range of 8-15 mA) can be applied to a target 602 for an extended period of time without blistering, or without substantial blistering. The extended period of time can be a proton fluence of, e.g., at least $6.3\pm0.6\times10^{20}$ p/cm$^{-2}$.

While not limited to such, in many example embodiments the lithium layer can be between 1-300 microns thick, and in some embodiments between 10 and 250 microns thick. While not limited to such, in many example embodiments a lithium compound layer, if present, can be between 1-500 microns thick, and in some embodiments between 10 and 300 microns thick, and in some embodiments between 15 and 100 microns thick. While not limited to such, in many example embodiments an amorphous portion of the substrate, if present, can be 1-500 microns thick, and in some embodiments between 10 and 300 microns thick, and in some embodiments between 15 and 100 microns thick. While not limited to such, in many example embodiments a substrate can be at least 100 microns thick, with the maximum thickness being dependent upon the application. In some embodiments the substrate is between 100 microns and 50 centimeters thick.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible.

In a first set of embodiments, a method of operating a beam system having a target that includes a lithium layer and a metallic substrate is provided, where the method includes: (a) subjecting the target to charged particle radiation such that the target emits neutrons and multiple blisters are formed in the target; and (b) subjecting the target to further charged particle radiation such that the target emits neutrons and the multiple blisters are reduced in quantity and/or size.

In some embodiments, the charged particle radiation is a proton beam.

In some embodiments, (b) subjecting the target to further charged particle radiation such that the target emits neutrons and the multiple blisters are reduced in quantity and/or size includes subjecting the target to a proton energy fluence of at least 0.5 times 1019 per square centimeter (cm−2).

In some embodiments, (b) subjecting the target to further charged particle radiation includes subjecting the target to further charged particle radiation until the quantity of blisters is reduced by an order of magnitude.

In some embodiments, neutrons are emitted at a first rate of at least 1 times 1012 neutrons per second in steps (a) and (b).

In some embodiments, (a) subjecting the target to charged particle radiation such that the target emits neutrons and multiple blisters are formed in the target further includes applying the emitted neutrons to a human patient.

In some embodiments, (b) subjecting the target to further charged particle radiation such that the target emits neutrons and the multiple blisters are reduced in quantity and/or size further includes applying the emitted neutrons to a human patient.

In some embodiments, the emitted neutrons are produced by the lithium layer according to the reaction p+7Li→n+ 7Be.

In some embodiments, the method further includes performing (a) and (b) as part of a boron neutron capture therapy (BNCT) procedure.

In some embodiments, the charged particle radiation is in the form of a beam, and where the target is subjected to the charged particle radiation in steps (a) and (b) while moving the beam across a surface of the target in a direction transverse to a direction of propagation of the beam.

In some embodiments, (b) further includes subjecting the target to further charged particle radiation such that the target emits neutrons and the multiple blisters are reduced in quantity and size.

In some embodiments, (b) further includes subjecting the target to further charged particle radiation such that the target emits neutrons and the multiple blisters are reduced in size only.

In some embodiments, the metallic substrate is copper. The lithium layer can be in contact with the copper substrate. The lithium layer can be formed directly on the copper bulk substrate.

In some embodiments, the lithium layer has a thickness in the range of 1 micron to 300 microns.

In some embodiments, the charged particle radiation has an energy in the range of 1.9 MeV-3.0 MeV.

In a second set of embodiments, a method of operating a beam system having a target that includes a lithium layer and a metallic substrate is provided, the method including: (a) subjecting the target to charged particle radiation such that the target emits neutrons and multiple blisters are formed in the target; and (b) subjecting the target to further charged particle radiation such that the target emits neutrons and a lithium compound layer forms between the lithium layer and the metallic substrate to a size sufficient to reduce the multiple blisters in quantity and/or size.

In some embodiments, the charged particle radiation is a proton beam.

In some embodiments, (b) subjecting the target to further charged particle radiation such that the target emits neutrons and the multiple blisters are reduced in quantity and/or size includes subjecting the target to a proton energy fluence of at least 0.5 times 1019 per square centimeter (cm−2).

In some embodiments, (b) subjecting the target to further charged particle radiation includes subjecting the target to further charged particle radiation until the quantity of blisters is reduced by an order of magnitude.

In some embodiments, neutrons are emitted at a first rate of at least 1 times 1012 neutrons per second in steps (a) and (b).

In some embodiments, (a) subjecting the target to charged particle radiation such that the target emits neutrons and multiple blisters are formed in the target further includes applying the emitted neutrons to a human patient.

In some embodiments, (b) subjecting the target to further charged particle radiation such that the target emits neutrons and the multiple blisters are reduced in quantity and/or size further includes applying the emitted neutrons to a human patient.

In some embodiments, the emitted neutrons are produced by the lithium layer according to the reaction p+7Li→n+7Be.

In some embodiments, the method further includes performing (a) and (b) as part of a boron neutron capture therapy (BNCT) procedure.

In some embodiments, the charged particle radiation is in the form of a beam, and where the target is subjected to the charged particle radiation in steps (a) and (b) while moving the beam across a surface of the target in a direction transverse to a direction of propagation of the beam.

In some embodiments, (b) further includes subjecting the target to further charged particle radiation such that the target emits neutrons and the multiple blisters are reduced in quantity and size.

In some embodiments, (b) further includes subjecting the target to further charged particle radiation such that the target emits neutrons and the multiple blisters are reduced in size only.

In some embodiments, the metallic substrate is copper and the lithium compound layer is a lithium copper compound.

In some embodiments, the lithium layer has a thickness in the range of 1 micron to 300 microns.

In some embodiments, the charged particle radiation has an energy in the range of 1.9 MeV-3.0 MeV.

In a third set of embodiments, a method of operating a beam system having a target that includes a lithium layer and a metallic substrate is provided, the method including: (a) subjecting the target to charged particle radiation such that the target emits neutrons and multiple blisters are formed in the target; and (b) subjecting the target to further charged particle radiation such that the target emits neutrons and the metallic substrate transitions from a crystalline state to an amorphous state sufficient to reduce the multiple blisters in quantity and/or size.

In some embodiments, the charged particle radiation is a proton beam.

In some embodiments, (b) subjecting the target to further charged particle radiation such that the target emits neutrons and the multiple blisters are reduced in quantity and/or size includes subjecting the target to a proton energy fluence of at least 0.5 times 1019 per square centimeter (cm−2).

In some embodiments, (b) subjecting the target to further charged particle radiation includes subjecting the target to further charged particle radiation until the quantity of blisters is reduced by an order of magnitude.

In some embodiments, neutrons are emitted at a first rate of at least 1 times 1012 neutrons per second in steps (a) and (b).

In some embodiments, (a) subjecting the target to charged particle radiation such that the target emits neutrons and multiple blisters are formed in the target further includes applying the emitted neutrons to a human patient.

In some embodiments, (b) subjecting the target to further charged particle radiation such that the target emits neutrons and the multiple blisters are reduced in quantity and/or size further includes applying the emitted neutrons to a human patient.

In some embodiments, the emitted neutrons are produced by the lithium layer according to the reaction p+7Li→n+7Be.

In some embodiments, the method further includes performing (a) and (b) as part of a boron neutron capture therapy (BNCT) procedure.

In some embodiments, the charged particle radiation is in the form of a beam, and where the target is subjected to the charged particle radiation in steps (a) and (b) while moving the beam across a surface of the target in a direction transverse to a direction of propagation of the beam.

In some embodiments, (b) further includes subjecting the target to further charged particle radiation such that the target emits neutrons and the multiple blisters are reduced in quantity and size.

In some embodiments, (b) further includes subjecting the target to further charged particle radiation such that the target emits neutrons and the multiple blisters are reduced in size only.

In some embodiments, (b) subjecting the target to further charged particle radiation further includes subjecting the target to further charged particle radiation such that a lithium compound layer forms between the lithium layer and the metallic substrate. The metallic substrate can be copper and the lithium compound layer can be a lithium copper compound. The step of (b) subjecting the target to further charged particle radiation can include subjecting the target to further charged particle radiation such that a lithium compound layer forms between the lithium layer and the metallic substrate to a depth that reaches or is adjacent to the multiple blisters.

In some embodiments, the lithium layer has a thickness in the range of 1 micron to 300 microns.

In some embodiments, the charged particle radiation has an energy in the range of 1.9 MeV-3.0 MeV.

In a fourth set of embodiments, a method is provided that includes: (a) subjecting a region of a metallic structure to charged particle radiation such that multiple deformations are formed in the region of the metallic structure, where the metallic structure includes a lithium layer; and (b) subjecting the region of the metallic structure to further charged particle radiation such that the multiple deformations are reduced in quantity and/or size.

In some embodiments, the charged particle radiation is a proton beam.

In some embodiments, (b) subjecting the region of the metallic structure to further charged particle radiation includes subjecting the region to further charged particle radiation until the quantity of deformations is reduced by an order of magnitude.

In some embodiments, the charged particle radiation is in the form of a beam, and where the region is subjected to the charged particle radiation in steps (a) and (b) while moving the beam across a surface of the region in a direction transverse to a direction of propagation of the beam.

In some embodiments, the metallic substrate is copper.

In some embodiments, the lithium layer is in contact with the copper substrate.

In some embodiments, the metallic structure is part of a plasma fusion reactor, and the charged particle radiation is emitted from the fusion reaction.

In some embodiments, the lithium layer has a thickness in the range of 1 micron to 300 microns.

In some embodiments, the deformations are blisters.

In some embodiments, (b) subjecting the region of the metallic structure to further charged particle radiation further includes subjecting the region to further charged particle radiation such that convective and/or capillary forces reduce the multiple deformations in quantity and/or size.

In a fifth set of embodiments, a method is provided that includes: (a) subjecting a region of a metallic structure to charged particle radiation such that multiple deformations are formed in the region of the metallic structure, where the metallic structure includes a lithium layer; and (b) subjecting the region of the metallic structure to further charged particle radiation such that a lithium compound layer forms between the lithium layer and the metallic substrate to a size sufficient to reduce the multiple deformations in quantity and/or size.

In some embodiments, the charged particle radiation is a proton beam.

In some embodiments, (b) subjecting the region to further charged particle radiation includes subjecting the region to further charged particle radiation until the quantity of blisters is reduced by an order of magnitude.

In some embodiments, the charged particle radiation is in the form of a beam, and where the region is subjected to the charged particle radiation in steps (a) and (b) while moving the beam across a surface of the region in a direction transverse to a direction of propagation of the beam.

In some embodiments, the metallic substrate is copper and the lithium compound layer is a lithium copper compound.

In some embodiments, the lithium layer has a thickness in the range of 1 micron to 300 microns.

In some embodiments, the deformations are blisters.

In a sixth set of embodiments, a method is provided that includes: (a) subjecting a region of a metallic structure to charged particle radiation such that multiple deformations are formed in the region of the metallic structure, where the metallic structure includes a lithium layer; and (b) subjecting the region of the metallic structure to further charged particle radiation such that the metallic substrate transitions from a crystalline state to an amorphous state sufficient to reduce the multiple deformations in quantity and/or size.

In some embodiments, the charged particle radiation is a proton beam.

In some embodiments, (b) subjecting the region to further charged particle radiation includes subjecting the region to further charged particle radiation until the quantity of blisters is reduced by an order of magnitude.

In some embodiments, the charged particle radiation is in the form of a beam, and where the region is subjected to the charged particle radiation in steps (a) and (b) while moving the beam across a surface of the region in a direction transverse to a direction of propagation of the beam.

In some embodiments, the metallic substrate is copper and the lithium compound layer is a lithium copper compound.

In some embodiments, the lithium layer has a thickness in the range of 1 micron to 300 microns.

In some embodiments, the deformations are blisters.

In some embodiments, (b) subjecting the region to further charged particle radiation further includes subjecting the region to further charged particle radiation such that a lithium compound layer forms between the lithium layer and the metallic substrate.

In some embodiments, the metallic substrate is copper and the lithium compound layer is a lithium copper compound.

In some embodiments, (b) subjecting the region to further charged particle radiation further includes subjecting the target to further charged particle radiation such that a lithium compound layer forms between the lithium layer and the metallic substrate to a depth that reaches or is adjacent to the multiple deformations.

In some embodiments, (b) subjecting the region of the metallic structure to further charged particle radiation further includes subjecting the region to further charged particle radiation such that convective and/or capillary forces reduce the multiple deformations in quantity and/or size.

In a seventh set of embodiments, a metallic body is provided that includes: a metallic substrate; and a layer including lithium coupled with the metallic substrate, where the metallic body has been exposed to a charged particle fluence of at least $6.3\pm0.6\times1020$ protons per square centimeter (p/cm−2).

In some embodiments, the metallic body exhibits a resistance to blister formation greater than the resistance to blister formation exhibited prior to the exposure.

In some embodiments, the metallic substrate includes copper.

In some embodiments, the metallic body further includes a lithium compound layer between the layer including lithium and the metallic substrate. The layer including lithium can include at least 90% lithium-7 isotope. The layer including lithium can include at least 98% lithium-7 isotope.

In some embodiments, a first portion of the metallic substrate is in an amorphous state. A second portion of the metallic substrate can be is in a crystalline state, where the first portion is relatively closer to the layer including lithium than the second portion.

In some embodiments, the metallic body is configured for use in a plasma fusion reactor.

In some embodiments, the metallic body is configured for use as a neutron generation target.

In an eighth set of embodiments, a metallic body is provided that includes: a metallic substrate; and a layer including lithium on the metallic substrate, where the metallic body has been exposed to charged particle radiation such that one or more blisters were first formed in the metallic body by the charged particle radiation and then the one or more blisters were reduced in size by the charged particle radiation.

In some embodiments, the metallic body exhibits a resistance to blister formation greater than the resistance to blister formation exhibited prior to the exposure.

In some embodiments, the metallic substrate includes copper.

In some embodiments, the metallic body further includes a lithium compound layer between the layer including lithium and the metallic substrate. The layer including lithium can include at least 90% lithium-7 isotope. The layer including lithium can include at least 98% lithium-7 isotope.

In some embodiments, a first portion of the metallic substrate is in an amorphous state. A second portion of the metallic substrate can be in a crystalline state, where the first portion is relatively closer to the layer including lithium than the second portion.

In some embodiments, the metallic body is configured for use in a plasma fusion reactor or as a neutron generation target.

In a ninth set of embodiments, a target for use in boron neutron capture therapy (BNCT) is provided where the target includes: a copper substrate; and a layer including lithium on the copper substrate, where the target has been exposed to charged particle radiation such that one or more blisters were first formed in the target by the charged particle radiation and then the one or more blisters were reduced in size by the charged particle radiation.

In some embodiments, the target exhibits a resistance to blister formation greater than the resistance to blister formation exhibited prior to the exposure.

In some embodiments, the lithium is in solid form.

In some embodiments, the lithium is in liquid form.

In some embodiments, the target is configured to generate neutrons when exposed to proton radiation having an average energy of 1.9 to 3.0 mega-electron-volts (MeV) and a current in the range of one to twenty milliamps (mA) until a proton fluence of at least 0.5 times 1019 per square centimeter (cm−2) occurs without substantial formation of blisters in the copper substrate. The target can be configured to generate neutrons according to the reaction p+7Li→n+7Be.

In a tenth set of embodiments, a target for use in boron neutron capture therapy (BNCT) is provided that includes: a first layer including lithium; a copper substrate; and a second layer including a lithium copper compound located between the first layer and the copper substrate, where the target is configured to generate neutrons when exposed to proton radiation.

In some embodiments, the target is configured to generate neutrons when exposed to proton radiation without substantial formation of blisters in the copper substrate.

In some embodiments, the target is configured to generate neutrons when exposed to proton radiation having an average energy of 1.9 MeV-3.0 MeV and a current in the range of 1-20 mA without substantial formation of blisters in the copper substrate.

In some embodiments, the target is configured to generate neutrons according to the reaction p+7Li→n+7Be.

In some embodiments, the lithium layer has a thickness in the range of 1 to 300 microns.

In an eleventh set of embodiments, a target for use in boron neutron capture therapy (BNCT) is provided that includes: a first layer including lithium; and a copper substrate having a first portion in an amorphous state, where the target is configured to generate neutrons when exposed to proton radiation.

In some embodiments, the target is configured to generate neutrons when exposed to proton radiation without substantial formation of blisters in the copper substrate.

In some embodiments, the target is configured to generate neutrons when exposed to proton radiation having an average energy of 1.9 MeV-3.0 MeV and a current in the range of 1-20 mA without substantial formation of blisters in the copper substrate.

In some embodiments, the target is configured to generate neutrons according to the reaction p+7Li→n+7Be.

In some embodiments, the first layer has a thickness in the range of 1 to 300 microns.

In some embodiments, a second portion of the copper substrate is in a crystalline state, where the first portion is relatively closer to the first layer including lithium than the second portion.

In some embodiments, the target further includes a lithium copper compound layer between the first layer and the copper substrate.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A method of operating a beam system having a target that comprises a lithium layer and a metallic substrate, the method comprising:
   (a) subjecting the target to charged particle radiation such that the target emits neutrons and a plurality of blisters are formed in the target; and (b) subjecting the target to further charged particle radiation such that the target emits neutrons and the plurality of blisters are reduced in quantity and/or size by subjecting the target to a proton energy fluence of at least $0.5$ times $10^{19}$ per square centimeter ($cm^{-2}$).

2. The method of claim 1, wherein the charged particle radiation is a proton beam.

3. The method of claim 1, wherein (b) subjecting the target to further charged particle radiation comprises subjecting the target to further charged particle radiation until the quantity of blisters is reduced by an order of magnitude.

4. The method of claim 1, wherein neutrons are emitted at a rate of at least 1 times $10^{12}$ neutrons per second in steps (a) and (b).

5. The method of claim 1, wherein (a) subjecting the target to charged particle radiation such that the target emits neutrons and a plurality of blisters are formed in the target further comprises applying the emitted neutrons to a human patient.

6. The method of claim 1, wherein (b) subjecting the target to further charged particle radiation such that the target emits neutrons and the plurality of blisters are reduced in quantity and/or size further comprises applying the emitted neutrons to a human patient.

7. The method of claim 1, wherein the emitted neutrons are produced by the lithium layer according to a reaction $p+^7Li \rightarrow n+^7Be$.

8. The method of claim 1, further comprising performing (a) and (b) as part of a boron neutron capture therapy (BNCT) procedure.

9. The method of claim 1, wherein the charged particle radiation is in the form of a beam, and wherein the target is subjected to the charged particle radiation in steps (a) and (b) while moving the beam across a surface of the target in a direction transverse to a direction of propagation of the beam.

10. The method of claim 1, wherein (b) further comprises subjecting the target to further charged particle radiation such that the target emits neutrons and the plurality of blisters are reduced in quantity and size.

11. The method of claim 1, wherein (b) further comprises subjecting the target to further charged particle radiation such that the target emits neutrons and the plurality of blisters are reduced in size only.

12. The method of claim 1, wherein the metallic substrate is a copper substrate and the lithium layer is in contact with the copper substrate.

13. The method of claim 12, wherein the lithium layer is in contact with the copper substrate.

14. The method of claim 1, wherein the lithium layer has a thickness in a range of 1 micron to 300 microns.

15. The method of claim 1, wherein the charged particle radiation has an energy in a range of 1.9 MeV-3.0 MeV.

16. The method of claim 1, wherein a lithium compound layer is formed between the lithium layer and the metallic substrate to a size sufficient to reduce the plurality of blisters in quantity and/or size.

17. A method of operating a beam system having a target that comprises a lithium layer and a metallic substrate, the method comprising:
(a) subjecting the target to charged particle radiation such that the target emits neutrons and a plurality of blisters are formed in the target; and
(b) subjecting the target to further charged particle radiation such that the target emits neutrons and the plurality of blisters are reduced in quantity and/or size, wherein neutrons are emitted at a rate of at least 1 times $10^{12}$ neutrons per second in steps (a) and (b).

18. The method of claim 17, wherein the charged particle radiation is a proton beam.

19. The method of claim 17, wherein (b) subjecting the target to further charged particle radiation comprises subjecting the target to further charged particle radiation until the quantity of blisters is reduced by an order of magnitude.

20. The method of claim 17, wherein (a) subjecting the target to charged particle radiation such that the target emits neutrons and a plurality of blisters are formed in the target further comprises applying the emitted neutrons to a human patient.

21. The method of claim 17, wherein (b) subjecting the target to further charged particle radiation such that the target emits neutrons and the plurality of blisters are reduced in quantity and/or size further comprises applying the emitted neutrons to a human patient.

22. The method of claim 17, wherein the emitted neutrons are produced by the lithium layer according to a reaction $p+^7Li \rightarrow n+^7Be$.

23. The method of claim 17, further comprising performing (a) and (b) as part of a boron neutron capture therapy (BNCT) procedure.

24. The method of claim 17, wherein the charged particle radiation is in the form of a beam, and wherein the target is subjected to the charged particle radiation in steps (a) and (b) while moving the beam across a surface of the target in a direction transverse to a direction of propagation of the beam.

25. The method of claim 17, wherein (b) further comprises subjecting the target to further charged particle radiation such that the target emits neutrons and the plurality of blisters are reduced in quantity and size.

26. The method of claim 17, wherein (b) further comprises subjecting the target to further charged particle radiation such that the target emits neutrons and the plurality of blisters are reduced in size only.

27. The method of claim 17, wherein the metallic substrate is a copper substrate and the lithium layer is in contact with the copper substrate.

28. The method of claim 17, wherein the lithium layer has a thickness in a range of 1 micron to 300 microns.

29. The method of claim 17, wherein the charged particle radiation has an energy in a range of 1.9 MeV-3.0 MeV.

30. The method of claim 17, wherein a lithium compound layer is formed between the lithium layer and the metallic substrate to a size sufficient to reduce the plurality of blisters in quantity and/or size.

31. The method of claim 17, wherein step (b) is performed by subjecting the target to a proton energy fluence of at least $0.5$ times $10^{19}$ per square centimeter ($cm^{-2}$).

32. A method of operating a beam system having a target that comprises a lithium layer and a metallic substrate, the method comprising:
(a) subjecting the target to charged particle radiation such that the target emits neutrons and a plurality of blisters are formed in the target; and
(b) subjecting the target to further charged particle radiation such that the target emits neutrons and the plurality of blisters are reduced in quantity and/or size, wherein the emitted neutrons are produced by the lithium layer according to a reaction $p+^7Li \rightarrow n+^7Be$.

33. The method of claim 32, wherein the charged particle radiation is a proton beam.

34. The method of claim 32, wherein (b) subjecting the target to further charged particle radiation comprises subjecting the target to further charged particle radiation until the quantity of blisters is reduced by an order of magnitude.

35. The method of claim 32, wherein (a) subjecting the target to charged particle radiation such that the target emits neutrons and a plurality of blisters are formed in the target further comprises applying the emitted neutrons to a human patient.

36. The method of claim 32, wherein (b) subjecting the target to further charged particle radiation such that the target emits neutrons and the plurality of blisters are reduced in quantity and/or size further comprises applying the emitted neutrons to a human patient.

37. The method of claim 32, further comprising performing (a) and (b) as part of a boron neutron capture therapy (BNCT) procedure.

38. The method of claim 32, wherein the charged particle radiation is in the form of a beam, and wherein the target is subjected to the charged particle radiation in steps (a) and (b) while moving the beam across a surface of the target in a direction transverse to a direction of propagation of the beam.

39. The method of claim 32, wherein (b) further comprises subjecting the target to further charged particle radiation such that the target emits neutrons and the plurality of blisters are reduced in quantity and size.

40. The method of claim 32, wherein (b) further comprises subjecting the target to further charged particle radiation such that the target emits neutrons and the plurality of blisters are reduced in size only.

41. The method of claim 32, wherein the metallic substrate is a copper substrate and the lithium layer is in contact with the copper substrate.

42. The method of claim 32, wherein the lithium layer has a thickness in a range of 1 micron to 300 microns.

43. The method of claim 32, wherein the charged particle radiation has an energy in a range of 1.9 MeV-3.0 MeV.

44. The method of claim 32, wherein a lithium compound layer is formed between the lithium layer and the metallic substrate to a size sufficient to reduce the plurality of blisters in quantity and/or size.

45. A method of operating a beam system having a target that comprises a lithium layer and a metallic substrate, the method comprising:
(a) subjecting the target to proton radiation such that the target emits neutrons and a plurality of blisters are formed in the target; and
(b) subjecting the target to further proton radiation such that the target emits neutrons and the plurality of blisters are reduced in quantity and/or size by subjecting the target to a proton energy fluence of at least 0.5 times $10^{19}$ per square centimeter ($cm^{-2}$),
wherein neutrons are produced by the lithium layer according to a reaction p+$^7$Li→n+$^7$Be and emitted at a rate of at least 1 times $10^{12}$ eutrons per second in steps (a) and (b).

46. The method of claim 45, wherein (b) subjecting the target to further proton radiation comprises subjecting the target to further proton radiation until the quantity of blisters is reduced by an order of magnitude.

47. The method of claim 45, wherein (a) subjecting the target to proton radiation such that the target emits neutrons and a plurality of blisters are formed in the target further comprises applying the emitted neutrons to a human patient.

48. The method of claim 45, wherein (b) subjecting the target to further proton radiation such that the target emits neutrons and the plurality of blisters are reduced in quantity and/or size further comprises applying the emitted neutrons to a human patient.

49. The method of claim 45, further comprising performing (a) and (b) as part of a boron neutron capture therapy (BNCT) procedure.

50. The method of claim 45, wherein the target is subjected to the proton radiation in steps (a) and (b) by moving a proton beam across a surface of the target in a direction transverse to a direction of propagation of the beam.

51. The method of claim 45, wherein (b) further comprises subjecting the target to further proton radiation such that the target emits neutrons and the plurality of blisters are reduced in quantity and size.

52. The method of claim 45, wherein (b) further comprises subjecting the target to further proton radiation such that the target emits neutrons and the plurality of blisters are reduced in size only.

53. The method of claim 45, wherein the metallic substrate is a copper substrate and the lithium layer is in contact with the copper substrate.

54. The method of claim 53, wherein the lithium layer was formed directly on the copper substrate.

55. The method of claim 45, wherein the lithium layer has a thickness in a range of 1 micron to 300 microns.

56. The method of claim 45, wherein the proton radiation has an energy in a range of 1.9 MeV-3.0 MeV.

57. The method of claim 45, wherein a lithium compound layer is formed between the lithium layer and the metallic substrate to a size sufficient to reduce the plurality of blisters in quantity and/or size.

* * * * *

UNITED STATES PATENT AND TRADEMARK OFFICE
CERTIFICATE OF CORRECTION

| | | |
|---|---|---|
| PATENT NO. | : 12,035,457 B2 | Page 1 of 1 |
| APPLICATION NO. | : 17/383188 | |
| DATED | : July 9, 2024 | |
| INVENTOR(S) | : Taskaev et al. | |

It is certified that error appears in the above-identified patent and that said Letters Patent is hereby corrected as shown below:

In the Claims

Column 30,
Line 5, in Claim 45, "eutrons" should read --neutrons--.

Signed and Sealed this
Fifth Day of August, 2025

Coke Morgan Stewart
*Acting Director of the United States Patent and Trademark Office*